US012694946B2

(12) United States Patent
Melnyk et al.

(10) Patent No.: US 12,694,946 B2
(45) Date of Patent: Jul. 28, 2026

(54) MACHINE LEARNING MODEL DISTILLATION FOR PROTEIN DESIGN

(71) Applicant: International Business Machines Corporation, Armonk, NY (US)

(72) Inventors: Igor Melnyk, White Plains, NY (US); Aurelie Chloe Lozano, Scarsdale, NY (US); Payel Das, New York, NY (US); Enara C. Vijil, Millwood, NY (US)

(73) Assignee: International Business Machines Corporation, Armonk, NY (US)

( * ) Notice: Subject to any disclaimer, the term of this patent is extended or adjusted under 35 U.S.C. 154(b) by 532 days.

(21) Appl. No.: 18/240,334

(22) Filed: Aug. 30, 2023

(65) Prior Publication Data

US 2025/0078953 A1 Mar. 6, 2025

(51) Int. Cl.
*G16B 15/20* (2019.01)
*G06N 20/00* (2019.01)
*G16B 15/30* (2019.01)
*G16B 40/20* (2019.01)

(52) U.S. Cl.
CPC ............. *G16B 15/20* (2019.02); *G06N 20/00* (2019.01); *G16B 15/30* (2019.02); *G16B 40/20* (2019.02)

(58) Field of Classification Search
CPC ........ G16B 15/20; G16B 15/30; G16B 40/20; G06N 20/00
See application file for complete search history.

(56) References Cited

U.S. PATENT DOCUMENTS

| | | | | |
|---|---|---|---|---|
| 11,545,238 B2 * | 1/2023 | Greving | ............. | G01N 33/6845 |
| 11,748,568 B1 * | 9/2023 | Orhan | ..................... | H04L 41/16 |
| | | | | 709/224 |
| 11,783,227 B2 * | 10/2023 | Li | ............................ | G06N 3/08 |
| | | | | 706/12 |
| 12,002,094 B2 * | 6/2024 | Kamkar | ................. | G06N 20/00 |
| 12,008,452 B2 * | 6/2024 | Nushi | .................... | G06N 5/045 |

(Continued)

FOREIGN PATENT DOCUMENTS

WO 2022167325 A1 8/2022

OTHER PUBLICATIONS

C. Hsu et a.l, "Learning inverse folding from millions of predicted structures," bioRxiv, Posted Sep. 6, 2022. https://doi.org/10.1101/2022.04.10.487779 22 pages.

(Continued)

*Primary Examiner* — David E Choi
(74) *Attorney, Agent, or Firm* — Seed Intellectual Property Law Group LLP

(57) ABSTRACT

A distilled machine learning model is produced via initializing a first model with initial weights. An input protein sequence is input into both the first model and a folding protein model, wherein the inputting to the first model generates logits, and wherein the inputting to the folding protein model generates one or more predictive metrics. The one or more predictive metrics are discretized into classes and a first cross-entropy loss is computed based on the logits and the classes. The first model is optimized based on the first cross-entropy loss so that the optimized first model is the distilled machine learning model and an additional machine learning model is trained, using the distilled machine learning model, to perform a downstream protein modeling task.

20 Claims, 14 Drawing Sheets

PDB ID 2qe9, Chain A

| | |
|---|---|
| TM | 0.98 |
| pTM (TM 42K) | 0.95 |
| pTM (TM 42K aug) | 0.85 |

(56) References Cited

U.S. PATENT DOCUMENTS

| 12,211,588 | B1 * | 1/2025 | Aithani | G16B 40/20 |
|---|---|---|---|---|
| 12,462,903 | B2 * | 11/2025 | Tonekaboni | G16C 20/70 |
| 2015/0356461 | A1 * | 12/2015 | Vinyals | G06N 20/20 |
| | | | | 706/12 |
| 2021/0027860 | A1 | 1/2021 | Zhang | |
| 2021/0209499 | A1 * | 7/2021 | Mishraky | G06N 20/00 |
| 2021/0304003 | A1 * | 9/2021 | Johnson | G06F 18/217 |
| 2021/0350819 | A1 * | 11/2021 | Wu | G06N 20/00 |
| 2022/0092366 | A1 * | 3/2022 | Chiu | G06N 3/0464 |
| 2022/0366263 | A1 * | 11/2022 | Ji | G06N 3/0895 |
| 2022/0375538 | A1 | 11/2022 | Das | |
| 2023/0031691 | A1 * | 2/2023 | Carroll | G06N 3/045 |
| 2023/0245722 | A1 * | 8/2023 | Liszka | C12N 15/625 |
| | | | | 706/25 |
| 2023/0325676 | A1 * | 10/2023 | Zhang | G06N 3/0464 |
| | | | | 706/25 |
| 2025/0006306 | A1 * | 1/2025 | Hoang | G16B 10/00 |
| 2025/0078953 | A1 * | 3/2025 | Melnyk | G06N 3/08 |
| 2025/0118391 | A1 * | 4/2025 | Yuan | G16B 35/20 |
| 2025/0322902 | A1 * | 10/2025 | Ramanathan | G16B 15/20 |
| 2025/0378364 | A1 * | 12/2025 | Tayeb | G06N 20/00 |

OTHER PUBLICATIONS

I. Melnyk et al., "AlphaFold Distillation for Improved Inverse Protein Folding," [Submitted on Oct. 5, 2022], https://arxiv.org/abs/2210.03488 Grace Period Disclosure 20 pages.

K. Yang et al., "Masked Inverse Folding with Sequence Transfer for Protein Representation Learning," bioRxiv, https://doi.org/10.1101/2022.05.25.493516, Posted Mar. 19, 2023. 18 pages.

M. Jendrusch et al., AlphaDesign: A de novo protein design framework based on AlphaFold. bioRxiv, Posted Oct. 12, 2021, https://doi.org/10.1101/2021.10.11.463937 20 pages.

P. Das, The Promise of Foundation Models and Generative AI, http://helper.ipam.ucla.edu/publications/ems2023/ems2023_18216.pdf 40 pages.

Z. Gao et al., "PiFold: Toward effective and efficient protein inverse folding," [Submitted on Sep. 22, 2022 (v1), last revised Jan. 12, 2023 (this version, v3)], https://arxiv.org/abs/2209.12643 14 pages.

Deep Mind, AlphaFold, 16 pages downloaded Jun. 27, 2023 from https://www.deepmind.com/research/highlighted-research/alphafold.

C. Hsu et a.l, "Learning inverse folding from millions of predicted structures," bioRxiv, Posted Sep. 6, 2022. https://doi.org/10.1101/2022.04.10.487779.

I. Melnyk et al., "AlphaFold Distillation for Improved Inverse Protein Folding," [Submitted on Oct. 5, 2022], https://arxiv.org/abs/2210.03488.

K. Yang et al., "Masked Inverse Folding with Sequence Transfer for Protein Representation Learning," bioRxiv, https://doi.org/10.1101/2022.05.25.493516, Posted Mar. 19, 2023.

M. Jendrusch et al., AlphaDesign: A de novo protein design framework based on AlphaFold. bioRxiv, Posted Oct. 12, 2021, https://doi.org/10.1101/2021.10.11.463937.

P. Das, The Promise of Foundation Models and Generative AI, http://helper.ipam.ucla.edu/publications/ems2023/ems2023_18216.pdf.

Z. Gao et al., "PiFold: Toward effective and efficient protein inverse folding," [Submitted on Sep. 22, 2022 (v1), last revised Jan. 12, 2023 (this version, v3)], https://arxiv.org/abs/2209.12643.

Alpha Fold can accurately predict 3D models of protein structures and is accelerating research in nearly every field of biology dowloaded from: https://www.deepmind.com/research/highlighted-research/alphafold Jun. 27, 2023 pp. 1-16.

Peter Mell and Timothy Grance, The NIST Definition of Cloud Computing, NIST Special Publication 800-145, Sep. 2011, cover, pp. i-iii and 1-3.

* cited by examiner

| Release 3 (January 2022) | | Release 4 (July 2022) | |
| --- | --- | --- | --- |
| Name | Size | Name | Size |
| Original | 907,578 | Original | 214,687,406 |
| TM 42K | 42,605 | pLDDT Balanced 1M | 1,000,000 |
| TM Augmented 86K | 86,811 | pLDDT Balanced 10M | 10,000,000 |
| pTM Synthetic 1M | 1,244,788 | pLDDT Balanced 60M | 66,736,124 |
| LDDT 42K | 42,605 | | |
| pLDDT 1M | 905,850 | | |

*FIG. 3A*

| Training Data | Validation CE Loss | Training Data | Validation CE Loss |
| --- | --- | --- | --- |
| TM 42K | 1.10 | LDDT 42K | 3.39 |
| TM Augmented 86K | 2.12 | pLDDT 1M | 3.24 |
| pTM Synthetic 1M | 2.55 | pLDDT Balanced 1M | 2.63 |
| | | pLDDT Balanced 10M | 2.43 |
| | | pLDDT Balanced 60M | 2.40 |

*FIG. 3B*

PDB ID 2qe9, Chain A

| TM | 0.98 |
|---|---|
| pTM (TM 42K) | 0.95 |
| pTM (TM 42K aug) | 0.85 |

PDB ID 1cw5, Chain A

| TM | 0.69 |
|---|---|
| pTM (TM 42K) | 0.74 |
| pTM (TM 42K aug) | 0.61 |

PDB ID 1hn3, Chain A

| TM | 0.38 |
| pTM (TM 42K) | 0.42 |
| pTM (TM 42K aug) | 0.46 |

Uniprot ID A0A7S0VSN1

Uniprot ID A0A539EBU7

Uniprot ID A0A5W8XA35

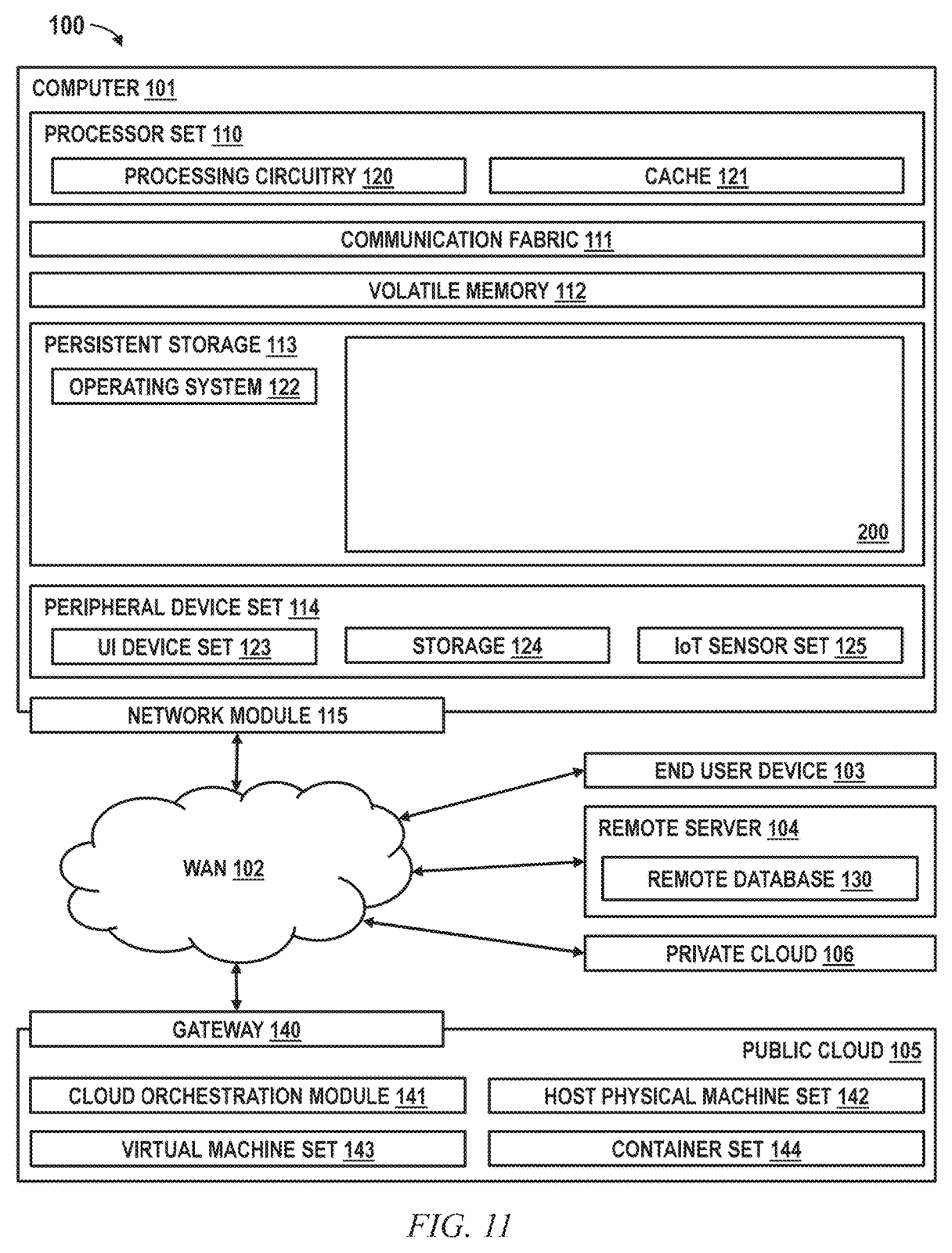

COMPUTER 101

PROCESSOR SET 110

| PROCESSING CIRCUITRY 120 | CACHE 121 |

COMMUNICATION FABRIC 111

VOLATILE MEMORY 112

PERSISTENT STORAGE 113

OPERATING SYSTEM 122

200

PERIPHERAL DEVICE SET 114

| UI DEVICE SET 123 | STORAGE 124 | IoT SENSOR SET 125 |

NETWORK MODULE 115

WAN 102

END USER DEVICE 103

REMOTE SERVER 104

REMOTE DATABASE 130

PRIVATE CLOUD 106

GATEWAY 140

PUBLIC CLOUD 105

| CLOUD ORCHESTRATION MODULE 141 | HOST PHYSICAL MACHINE SET 142 |
| VIRTUAL MACHINE SET 143 | CONTAINER SET 144 |

*FIG. 11*

MACHINE LEARNING MODEL DISTILLATION FOR PROTEIN DESIGN

BACKGROUND

The present invention relates generally to the electrical, electronic and computer arts and, more particularly, to machine learning and pharmaceuticals.

SUMMARY

Principles of the invention provide systems and techniques for machine learning model distillation for protein design. In one aspect, an exemplary method includes the operations of producing a distilled machine learning model via: initializing a first model with initial weights; inputting an input protein sequence into both the first model and a folding protein model, wherein the inputting to the first model generates logits, and wherein the inputting to the folding protein model generates one or more predictive metrics; discretizing the one or more predictive metrics into classes; computing a first cross-entropy loss based on the logits and the classes; and optimizing the first model based on the first cross-entropy loss so that the optimized first model is the distilled machine learning model; and training, using the distilled machine learning model, an additional machine learning model to perform a downstream protein modeling task.

In one aspect, a computer program product comprises one or more tangible computer-readable storage media and program instructions stored on at least one of the one or more tangible computer-readable storage media, the program instructions executable by a processor to cause the processor to perform operations comprising producing a distilled machine learning model via: initializing a first model with initial weights; inputting an input protein sequence into both the first model and a folding protein model, wherein the inputting to the first model generates logits, and wherein the inputting to the folding protein model generates one or more predictive metrics; discretizing the one or more predictive metrics into classes; computing a first cross-entropy loss based on the logits and the classes; and optimizing the first model based on the first cross-entropy loss so that the optimized first model is the distilled machine learning model; and training, using the distilled machine learning model, an additional machine learning model to perform a downstream protein modeling task.

In one aspect, an apparatus comprises a memory and at least one processor, coupled to the memory, and operative to perform operations comprising producing a distilled machine learning model via: initializing a first model with initial weights; inputting an input protein sequence into both the first model and a folding protein model, wherein the inputting to the first model generates logits, and wherein the inputting to the folding protein model generates one or more predictive metrics; discretizing the one or more predictive metrics into classes; computing a first cross-entropy loss based on the logits and the classes; and optimizing the first model based on the first cross-entropy loss so that the optimized first model is the distilled machine learning model; and training, using the distilled machine learning model, an additional machine learning model to perform a downstream protein modeling task.

As used herein, "facilitating" an action includes performing the action, making the action easier, helping to carry the action out, or causing the action to be performed. Thus, by way of example and not limitation, instructions executing on a processor might facilitate an action carried out by instructions executing on a remote processor (e.g., controlling chemical processing equipment to synthesize molecules or the like), by sending appropriate data or commands to cause or aid the action to be performed. Where an actor facilitates an action by other than performing the action, the action is nevertheless performed by some entity or combination of entities.

These and other features and advantages will become apparent from the following detailed description of illustrative embodiments thereof, which is to be read in connection with the accompanying drawings.

BRIEF DESCRIPTION OF THE DRAWINGS

The following drawings are presented by way of example only and without limitation, wherein like reference numerals (when used) indicate corresponding elements throughout the several views, and wherein:

FIG. 3A presents database statistics useful in connection with aspects of the invention;

FIG. 3B is a table showing the validation cross-entropy (CE) loss for a variety of example datasets, in accordance with an example embodiment;

FIG. 8A shows representations of the diversity of amino acids for a set of proteins for the conventional inverse protein folding task of FIG. 7, produced with conventional baseline geometric vector perceptrons (GVP);

FIG. 8B shows representations of the diversity of amino acids for a set of proteins for the conventional inverse protein folding task of FIG. 7, produced with conventional baseline geometric vector perceptrons (GVP) enhanced with structure consistency-regularization in accordance with an example embodiment;

FIG. 11 depicts a computing environment according to an embodiment of the present invention.

Figures 1A, 1B:
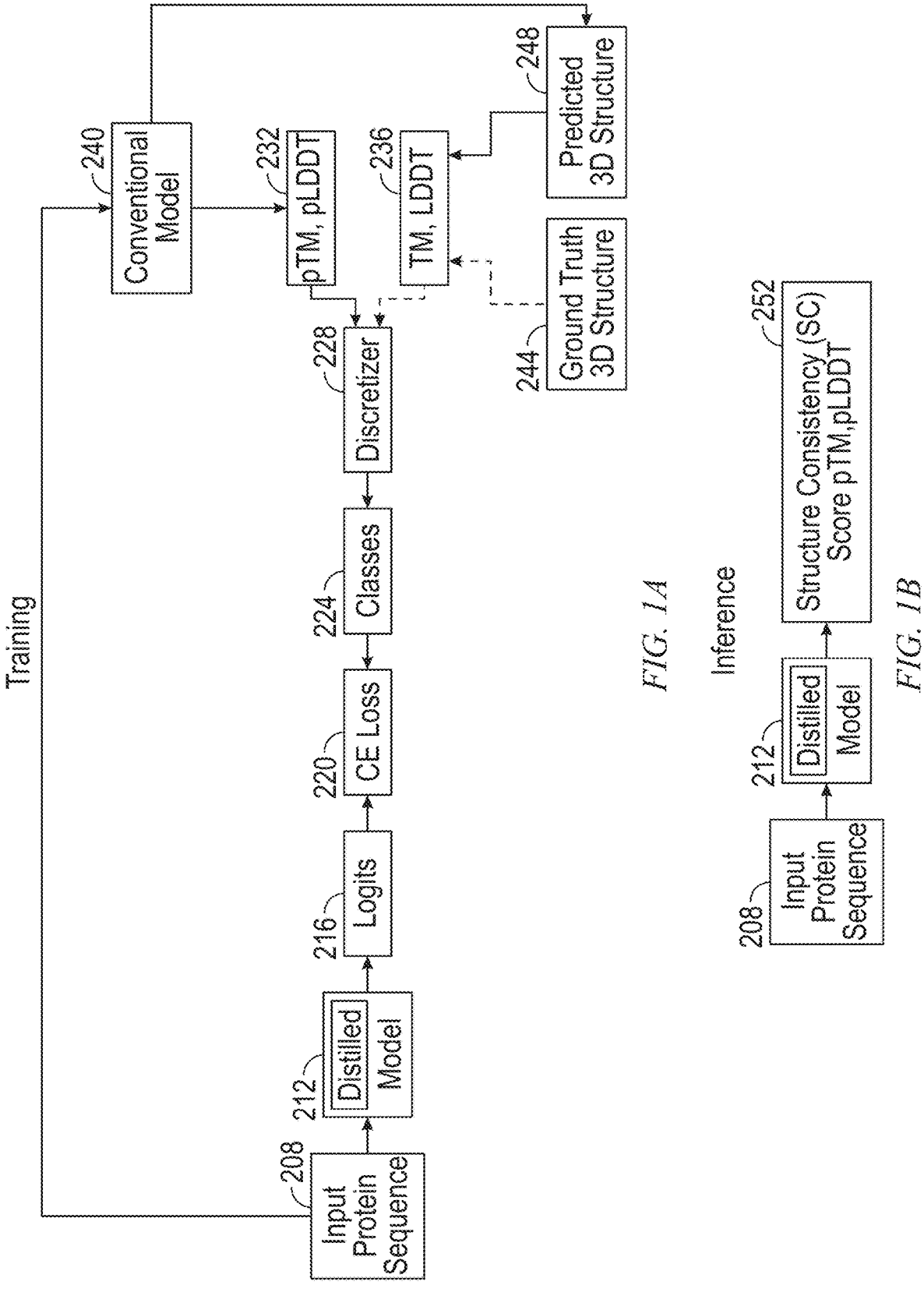
FIG. 1A is a block diagram of a system for generating a distilled model, in accordance with an example embodiment.
FIG. 1B is block diagram of a system for utilizing the distilled model to generate a structure consistency (SC) score for a given input protein sequence, in accordance with an example embodiment.

It is to be appreciated that elements in the figures are illustrated for simplicity and clarity. Common but well-understood elements that may be useful or necessary in a commercially feasible embodiment may not be shown in order to facilitate a less hindered view of the illustrated embodiments.

DETAILED DESCRIPTION

Principles of inventions described herein will be in the context of illustrative embodiments. Moreover, it will become apparent to those skilled in the art given the teachings herein that numerous modifications can be made to the embodiments shown that are within the scope of the claims. That is, no limitations with respect to the embodiments shown and described herein are intended or should be inferred.

Generally, techniques are disclosed for evaluating a candidate protein, such as evaluating the viability of the protein. In one example embodiment, a quality metric is defined that quantifies the quality (such as the viability) of the protein. For example, the metric may indicate the likelihood that the sequence can be folded into a 3D structure.

Protein pharmaceuticals are large molecules with hundreds of amino acids. In general, proteins are sequences of amino acids (the building blocks of proteins) ranging from about twenty to 1,000 amino acids. Scientists often attempt to generate new sequences of amino acids to identify or create new proteins. An important step in creating a new protein is determining whether a proposed sequence is viable, such as whether the sequence has certain properties, whether the sequence can be folded into a viable three-dimensional (3D) structure, and the like. This step is often accomplished via, for example, biological testing. Pretrained artificial intelligence (AI) models may also be used to determine whether a proposed sequence is viable.

Moreover, a variety of tasks are important for the creation and identification of proteins. Given a sequence of amino acids, forward protein folding derives the corresponding 3D structure of the sequence. Given a 3D structure, inverse protein folding derives the corresponding sequence of amino acids. These tasks are fundamental challenges in, for example, bioengineering and drug discovery.

Inverse protein folding, that is, designing sequences that fold into a given three-dimensional structure, is one of the fundamental design challenges in bio-engineering and drug discovery. Traditionally, inverse folding mainly involves learning from sequences that have an experimentally resolved structure. However, the known structures cover only a tiny space of the protein sequences, imposing limitations on the model learning. Recently, proposed forward folding models offer unprecedented opportunity for accurate estimation of the structure given a protein sequence. Incorporating a forward folding model as a component of an inverse folding approach would offer the potential of significantly improving the inverse folding, as the folding model can provide feedback on any generated sequence in the form of the predicted protein structure or a structural confidence metric. At present, however, these forward folding models are still prohibitively slow to be a part of the model optimization loop during training. In example embodiments, knowledge distillation is performed on the folding model's confidence metrics to obtain a smaller, faster and end-to-end differentiable distilled model, which can then be included as part of the structure consistency regularized inverse folding model training. Moreover, the disclosed regularization technique is general enough that it can be applied in other design tasks, such as sequence-based protein infilling. Extensive experiments show a clear benefit of the disclosed inventive methods over the non-regularized baselines. For example, in inverse folding design problems, an up to 3% improvement in sequence recovery and up to 45% improvement in protein diversity was observed, while still preserving the structural consistency of the generated sequences.

Introduction

Numerous top selling drugs are engineered proteins. For functional protein design, it is often a prerequisite that the designed protein folds into a specific three-dimensional structure. The fundamental task of designing novel amino acid sequences that will fold into the given 3D protein structure is named inverse protein folding. Inverse protein folding is therefore a central challenge in bio-engineering and drug discovery.

Computationally, inverse protein folding can be formulated as exploring the protein sequence landscape for a given protein backbone to find a combination of amino acids that supports a property (such as structural consistency). Computational protein design has traditionally been handled by learning to optimize amino acid sequences against a physics-based scoring function. In recent years, deep generative models have been proposed to solve this task, which includes learning a mapping from protein structure to sequences. These approaches frequently use high amino acid recovery with respect to the ground truth sequence (corresponding to the input structure) as one success criterion. Other success criteria are a high template modeling (TM) score (reflecting structural consistency) and low perplexity (measuring likelihood to the training/natural sequence distribution). However, such criteria solely ignore the practical purpose of inverse protein folding, that is, to design novel and diverse sequences that fold to the desired structure and thus exhibit novel functions.

In parallel to machine learning advances in inverse folding, notable progress has been made recently in protein representation learning, protein structure prediction from sequences, as well as in conditional protein sequence generation. These lines of work have largely benefited by learning from millions of available protein sequences (that may or may not have a resolved structure) in a self/unsupervised pretraining paradigm. Such large-scale pre-training has immensely improved the information content and task performance of the learned model. For example, it has been observed that structural and functional aspects emerge from a representation learned on broad protein sequence data. In contrast, inverse protein folding has mainly focused on learning from sequences that do have an experimentally resolved structure. Those reported structures cover only less than 0.1% of the known space of protein sequences, limiting the learning of the inverse folding model. In this direction, a recent work has trained an inverse folding model from scratch on millions of predicted protein structures (in addition to tens of thousands of experimentally resolved structures) and shown performance improvement in terms of amino acid recovery. However, such large-scale training from scratch is computationally expensive. The present inventive embodiments are built on a finding that a more efficient alternative is to use the guidance of an already available forward folding model pretrained on large-scale data in training the inverse folding model.

In one example embodiment, a framework is established where the inverse folding model is trained using a loss objective that includes a regular sequence reconstruction loss, augmented with an additional structure consistency loss (SC). In one example embodiment, a conventional forward protein folding model is used to estimate the protein structure from a generated sequence, the estimated protein structure is compared with ground truth, and a TM score is computed to regularize the training. However, a challenge in using a conventional forward protein folding model directly is the computational cost associated with its inference, as well as the need for a ground truth reference structure. In one example embodiment, internal confidence structure metrics from the conventional forward folding model are used instead. However, this approach is still slow for the in-the-loop inverse folding model optimization. To address these issues, in example embodiments, knowledge distillation is performed using a conventional forward folding model and a resulting distilled model is included as part of the regularized training of the inverse folding model (this is termed a structure consistency (SC) loss). The main properties of the distilled model are that it is fast, accurate and end-to-end differentiable. Extensive evaluations were performed, where the results on standard structure-guided sequence design benchmarks show that exemplary embodiments outperform existing baselines in terms of lower perplexity and higher amino acid recovery, while maintaining closeness to original protein structure. More interestingly, diversity in the designed sequences is improved, one of the main goals of protein design. As a result of a trade-off between sequence recovery vs. structure recovery, an exemplary regularized model yields better sequence diversity for a given structure, consistent with the fact that even a small (35-40 amino acid) protein fold holds a 'sequence capacity' exceeding 1023. Note that exemplary embodiments are not limited to the inverse folding design and, as is shown, can be applied to other applications, such as sequence-based protein infilling, where performance improvement over the baseline is also observed. In addition, the estimated structure consistency metric can be used as part of the regularization of an inverse folding task, an infilling task, during any other protein optimization tasks which would benefit from structural consistency estimation of the designed protein sequence, and/or as an inexpensive surrogate of a larger conventional inverse folding model that provides scoring of a given protein, reflecting its structural content.

In one example embodiment, an exemplary machine learning tool is utilized to improve other machine learning tools that are tailored, for example, towards the design of proteins. For example, machine learning may be used to perform inverse protein folding and translate a 3D protein structure to a sequence of amino acids (also referred to as a sequence herein). The number of known 3D protein structures available for training is, however, limited. As a result, conventional inverse protein folding techniques often fail to design novel and diverse sequences that fold into a viable structure.

In one example embodiment, knowledge distillation is used to generate a machine learning model that generates a metric that quantifies the quality (such as the viability) of a protein sequence. The machine learning model is distilled from, for example, a large conventional forward protein folding model. The distilled machine learning model is smaller than, and runs faster than, the larger model from which it is distilled. The smaller model refers to having fewer layers, fewer dimensions, and/or fewer neural network connections than the larger model has.

Traditionally, the distillation process would be done using soft labels, which are probabilities from the large conventional forward protein folding model, and hard labels, which are the ground truth classes. In one example embodiment, the probabilities are not used as they are often harder to collect or are unavailable; instead, the predictions of the large conventional forward protein folding model and the hard labels (the TM/LDDT scores) computed based on the predicted 3D structures of the large conventional forward protein folding model are used.

In one example embodiment, the conventional forward protein folding model is capable of accurately estimating a 3D structure for a given amino acid sequence and also providing predicted and/or actual value confidence metrics (such as a predictive Local Distance Difference Test (pLDDT), a predictive template modeling (pTM) metric, and actual values for each of the foregoing metrics), but can be very slow to run (such as needing ~30 seconds per sequence). The conventional forward protein folding model is also not suitable for, for example, an end-to-end training process of other machine learning models, such as an inverse protein folding model. (The TM metric is the mean distance between structurally aligned Ca atoms scaled by a length-dependent distance parameter. The LDDT (Local Distance Difference Test) metric is the average of four fractions computed using distances between all pairs of atoms based on four tolerance thresholds (0.5 Angstroms (Å), 1 Å, 2 Å, 4 Å) within 15 Å inclusion radius. The range of both metrics is (0,1), and the higher values represent more similar structures. It is noted that the template modeling (TM) metric is a single scalar value whereas the Local Distance Difference Test (LDDT) metric assigns a number to each position of an amino acid in the protein sequence, where the number indicates how well the amino acid in each position of the protein matches the amino acid in the corresponding position of a ground truth protein. If the metrics are relatively small (indicating a large discrepancy), then the protein sequence is interpreted as being of lower quality with a lower likelihood of being foldable into a 3D structure. If the metrics are relatively large (indicating a small discrepancy), then the protein sequence is interpreted as being higher quality with a higher likelihood of being foldable into a 3D structure).

Knowledge Distillation

In one example embodiment, the larger conventional forward protein folding model is distilled into a smaller, faster, differentiable model suitable for, for example, an end-to-end training process and for improving other tasks, such as training an inverse protein folding model. In one example embodiment, the distilled model is trained on data generated by the conventional forward protein folding model, such as the (p)TM/(p) LDDT scores generated from a corresponding input sequence. In one example embodiment, the distilled model is deployed as part of an optimization loop for training the inverse protein folding model or other downstream task. More generally, the distilled model may be used in any protein optimization algorithm. (It is noted that pTM and pLDDT are the predicted metrics of the large conventional forward protein folding model for a given input protein sequence, corresponding to the reconstructed 3D protein structure, which represent the model's confidence of the estimated structure. pLDDT is a local per-residue score (pLDDT chain is another score that simply averages per-residue pLDDTs across the chain), while pTM is a global confidence metric for assessing the overall chain reconstruction. These metrics are interpreted as the quality or validity of the sequence for the purpose of downstream applications.)

FIG. 1A is a block diagram of a system for generating a distilled model 212, in accordance with an example embodiment. In one example embodiment, the distilled model 212 is initialized with weights based on a conventional protein bidirectional encoder representation for transformers (BERT) model (a model that was pretrained on a large corpus of protein sequences, also referred to as conventional protein version of a BERT model herein), although the distilled model 212 may be initialized via other techniques, including being initialized with random weights. (It is noted that the head of a conventional protein version of a BERT model was modified by setting the vocabulary size to 50, corresponding to discretizing pTM/pLDDT in the range (0,1). For the pTM (scalar), the output corresponds to the first (Cardiolipin synthase (CLS)) token of the output sequence, while for the pLDDT (sequence), the predictions are made for each residue position.) A set of input protein sequences 208 is submitted to the distilled model 212 which generates a set of logits 216 (i.e., the unnormalized outputs of a neural network that are produced before the application of a softmax function). The set of input protein sequences 208 is also submitted to the conventional forward protein folding model 240 which generates a predicted 3D structure 248 for the submitted input protein sequence 208, as described above. (It is noted that, in one example embodiment, the input protein sequences 208 are submitted sequentially to both models 212, 240.) The conventional forward protein folding model 240 also generates predicted metrics 232 (such as the pLDDT and pTM metrics, where the "p" stands for predictive and which, as described above, quantify the quality of the corresponding protein.) Since the generated pLDDT metrics are continuous values ranging from zero to one, a discretizer 228 is used to discretize the pLDDT metric, such as by classifying the values into classes 224 based on a number of bins (corresponding to discretized value ranges). In one example embodiment, 50 bins are defined. The number of bins may be selected heuristically by, for example, using the information from a histogram of the values to discretized.

A cross-entropy (CE) loss 220 is then computed based on the target classes 224 and the logits 216. If there is no mismatch between the target classes 224 and the logits 216, there is no loss, the accuracy of the distilled model 212 is assumed to be satisfactory, and the training of the distilled model 212 is ended; otherwise, training continues to minimize the CE loss 220. In one example embodiment, in computing the CE loss 220, a set of sequences 208 is processed and the results are averaged to compute the CE loss 220. In one example embodiment, the set of sequences 208 includes 16 or 32 sequences.

Since the metrics predicted by the conventional forward protein folding model 240 (pLDDT and pTM) may be relatively inaccurate, an alternate method may be used to generate the classes 224. The predicted 3D protein structure 248 generated by the conventional forward protein folding model 240 is compared with a 3D ground truth structure 244, if available, that corresponds to the input protein sequence 208. (It is noted that the number of available 3D ground truth structures 244 is typically limited.) In this case, the metrics 236, such as Local Distance Difference Test (LDDT) and template modeling (TM), are the actual values (not predicted values) and are therefore generally more accurate than the predicted metrics 232. In one example embodiment, the metrics 236 are generated if a 3D ground truth structure 244 corresponding to the input protein sequence 208 is available and predicted metrics are generated if a 3D ground truth structure 244 corresponding to the input protein sequence 208 is not available.

FIG. 1B is block diagram of a system for utilizing the distilled model 212 to generate a structure consistency (SC) score 252 for a given input protein sequence 208, in accordance with an example embodiment. The trained distilled model 212 generates a structure consistency (SC) score 252 for each submitted input protein sequence 208. As described above, the trained distilled model 212 is a smaller model than the conventional forward protein folding model 240 and generates the structure consistency (SC) score 252 faster than the conventional forward protein folding model 240. As illustrated in FIG. 1B, the structure consistency (SC) score 252 includes the pTM and pLDDT metrics.

As described above, the metrics TM and LDDT quantify the difference between the ground truth 3D structure 244 and the predicted 3D structure 248 whereas the predicted metrics 232 (pTM and pLDDT) are a predicted version of the cited difference. If the metrics 232, 236 are relatively small (indicating a large discrepancy), then the input protein sequence 208 is interpreted as being of lower quality with a lower likelihood of being foldable into a 3D structure. If the metrics are relatively large (indicating a small discrepancy), then the input protein sequence 208 is interpreted as being higher quality with a higher likelihood of being foldable into a 3D structure.

Data

Figure 2A:
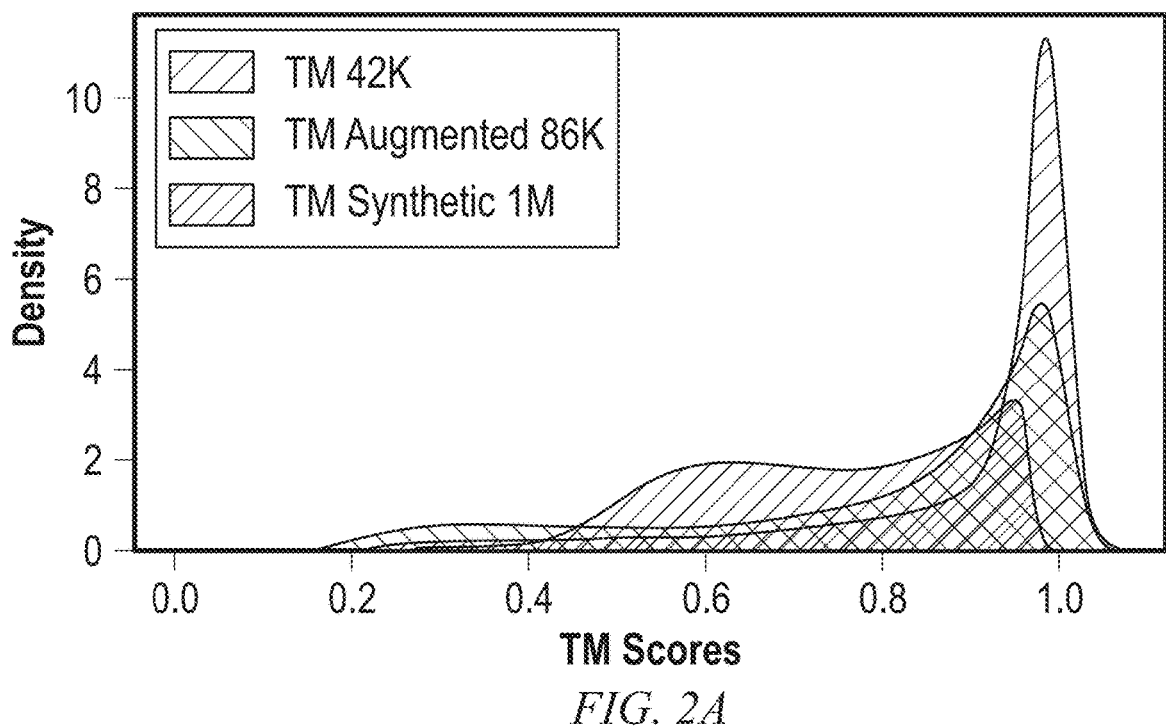
FIGS. 2A-2B are graphical visualizations of the distribution of example metric scores obtained in experiments, in accordance with an example embodiment.
Figure 2B:
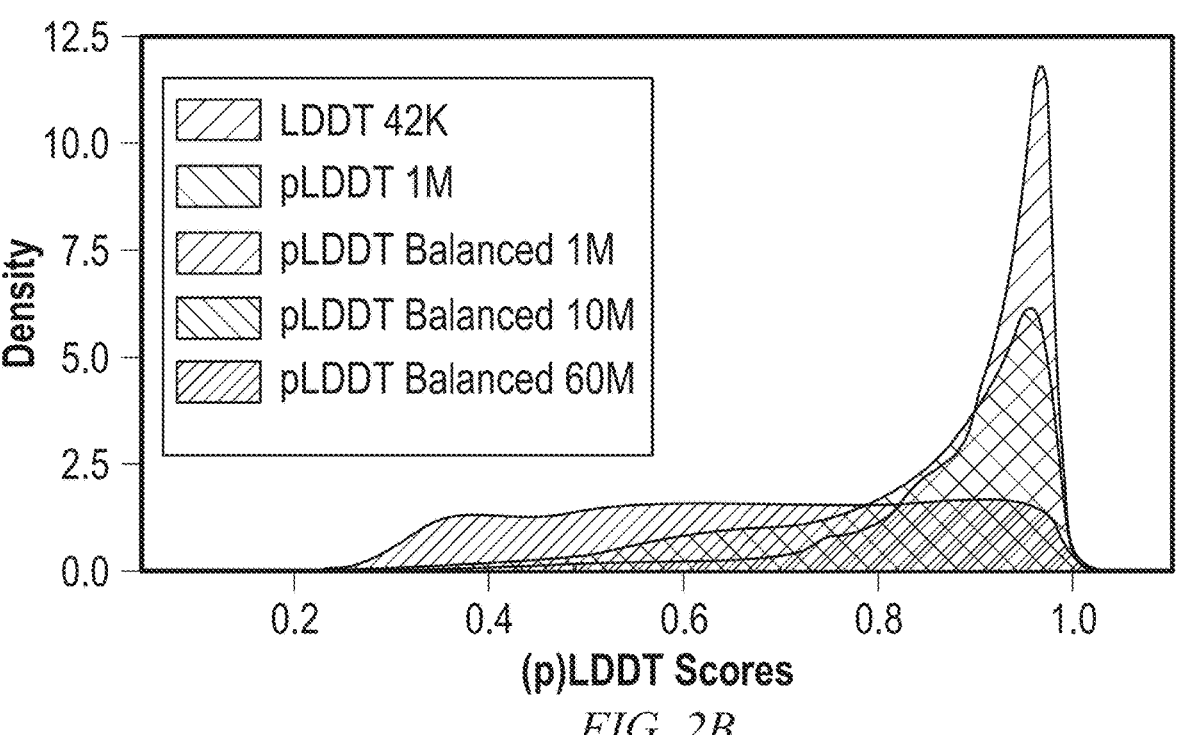

FIGS. 2A-2B are graphical visualizations of the distribution of example metric scores obtained in experiments, on datasets that were used to help train the distilled model, e.g., as shown in FIG. 1A, in accordance with an example embodiment. The experiments were conducted using conventional datasets (including experimentally-verified datasets), synthetic datasets (including unverified synthetic datasets), augmented datasets (conventional datasets augmented with samples to broadly distribute the levels of quality, including conventional datasets augmented with synthetic examples), and the like. A set of 907,578 predicted structures was collected using the large conventional forward protein folding model. Each of these predicted structures contains 3D coordinates of all the residue atoms as well as the per-residue pLDDT confidence scores. To avoid any data leakage to the downstream applications, the structures that are part of the validation were filtered out and test splits of a classification of protein structures dataset were tested (discussed in the section entitled "Inverse Protein Folding Design"). Then, using the remaining structures, the pLDDT 1M dataset was created (see table of FIG. 3A), where each protein sequence is paired with the sequence of per-residue pLDDTs. Proteins up to length 500 were also truncated to reduce computational complexity of the training of the distilled model.

Datasets which are based on the true TM and LDDT values were also created using the predicted structures of the large conventional forward protein folding model. Specifically, using a mapping of a comprehensive and constantly updated collection of experimentally determined 3D structures of proteins and sequences to a collection of protein sequence and functional information from a wide range of organisms (sequences only), a subset of samples with matching ground truth sequences and 3D structures were selected from the former collection, resulting in 42,605 structures. These datasets are denoted as TM 42K and LDDT 42K (see table of FIG. 3A). In FIGS. 2A-2B, the score density distribution of each dataset is shown. As can be seen, the TM 42K and LDDT 42K are very skewed to the upper range of the values. To mitigate this data imbalance, two additional TM-based datasets were curated. The TM augmented 86K dataset was obtained by augmenting the TM 42K dataset with a set of perturbed original protein sequences, estimating their structures with the large conventional forward protein folding model, computing corresponding TM-score, and keeping the low and medium range TM values. The pTM synthetic 1M dataset was obtained by generating random synthetic protein sequences and feeding them to the distilled model 212 (pre-trained on the TM 42K dataset) to generate additional data samples and collect lower-range pTM values. These curated datasets are examples of using computer-generated protein sequences as training data (as items 208) for helping to train the distilled model 212. The distribution of the scores for these additional datasets is also shown in FIGS. 2A-2B, where both the TM augmented 86K and pTM synthetic 1M datasets (labeled as "TM Synthetic 1M" in FIG. 2A) are less skewed, covering lower (p)TM values better.

In addition, a distribution density of pLDDT values was plotted using over 214M predicted structures and a similar high skewness towards upper range was observed. To fix this, the data was rebalanced by filtering out samples with upper-range mean-pLDDT values (also called pLDDT chain). The resulting dataset contains 60M sequences, for which 10M and 1M versions were additionally created (see FIGS. 2A-2B for their density).

As illustrated in FIGS. 2A-2B, the scores obtained for some datasets are biased towards a score of 1.0, meaning the protein sequences of the corresponding dataset are of relatively high quality. While this represents quality protein sequences, the corresponding dataset may be a poor training dataset, as the distilled model 212 will assume that most encountered protein sequences are also of high quality during training and, during inferencing, may mislabel some protein sequences accordingly. A superior training dataset will have a broader uniform distribution of the quality scores, as with the TM synthetic 1M dataset of FIG. 2A and the pLDDT balanced 1M dataset, the pLDDT balanced 10M dataset, and the pLDDT balanced 60M dataset of FIG. 2B. (It is noted that the number in the title of the dataset is the number of samples in the dataset.) FIG. 3A also shows database statistics related to these training datasets that are discussed.

Experimental Results

Evaluation results of the distilled model 212 after training it on the presented datasets are described herein. It is noted that, to further improve the data imbalance problem, during training, the weighted sampling that was employed in the minibatch generation (using a loss function that assigns higher weights to challenging examples during training to address class imbalance and improve the performance of object detection and multi-class classification models) was also used in place of the traditional cross-entropy loss. The results for (p)TM-based datasets are shown in the table of FIG. 3B. It is seen that the distilled model 212 trained on the TM 42K dataset performed the best, followed by the dataset with the augmentations, and the synthetic data. For the (p)

LDDT-based datasets, it was observed that increasing the scale coupled with the data balancing improves the validation performance.

Figure 3C:
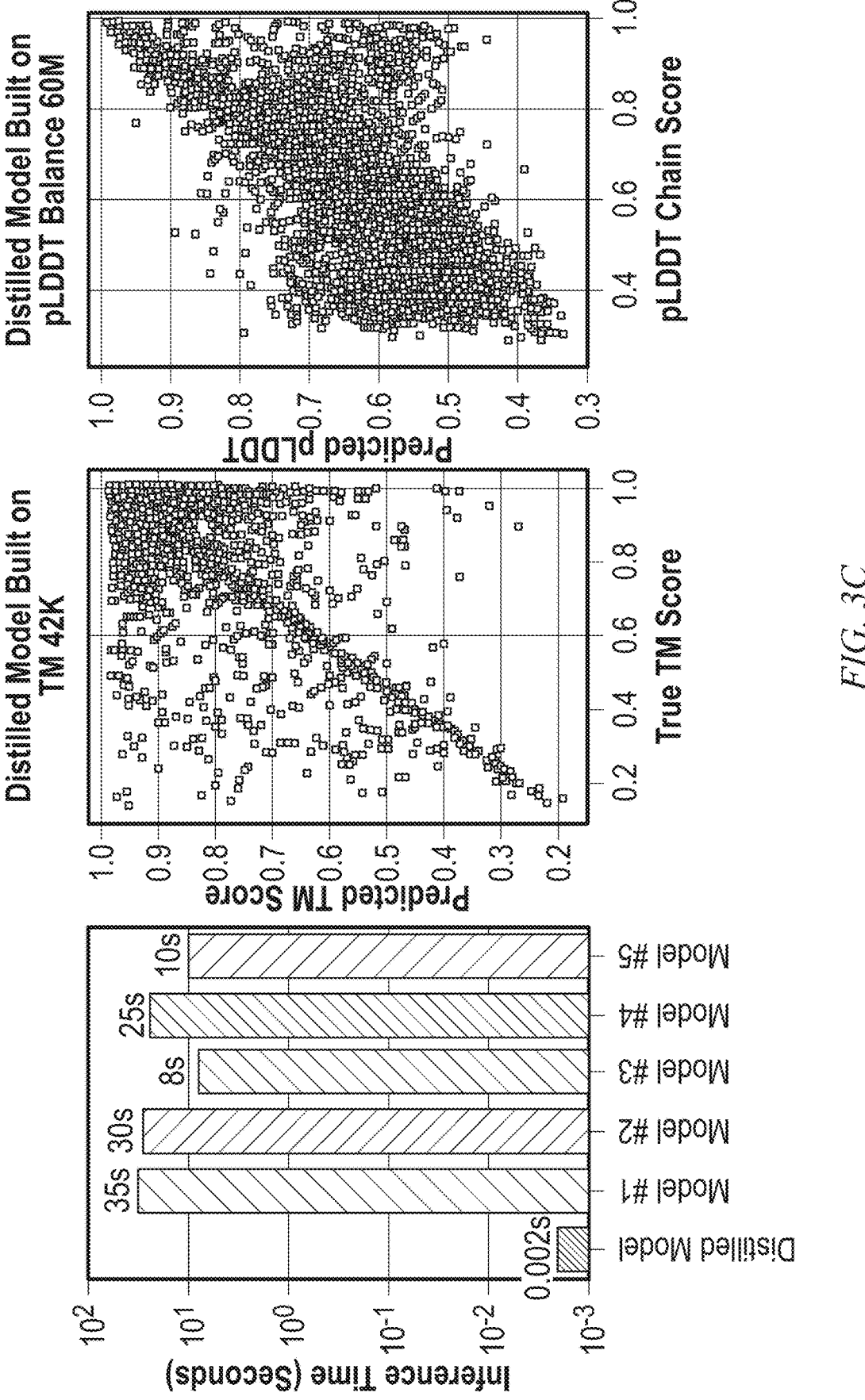
FIG. 3C shows the average inference time for a protein sequence of length 500 by the distilled model versus the alternatives (left plot), in accordance with an example embodiment.

FIG. 3C shows the average inference time for a protein sequence of length 500 by the distilled model 212 versus the alternatives (left plot in FIG. 3C) and scatter plots (center and right plots in FIG. 3C) of the true TM score vs pTM scores and pLDDT values on the entire validation set, in accordance with an example embodiment. The timings for the large conventional forward protein folding model and a second large conventional forward protein folding model exclude the multiple sequence alignment (MSA) searching time, which can vary from a few minutes to a few hours. As can be seen, the inference time of the current alternatives is too slow, which makes them impractical to be included as part of the model optimization loop. On the other hand, the distilled model 212 is fast, accurate and end-to-end differentiable. The middle plot shows the true TM score and the distilled model 212 predicted TM scores on TM distillation datasets (Pearson's correlation is 0.77). The right plot shows a similar scatter plot of the (averaged) true and the predicted pLDDT values on the pLDDT distillation dataset (Pearson's correlation is 0.76).

Figure 4A:
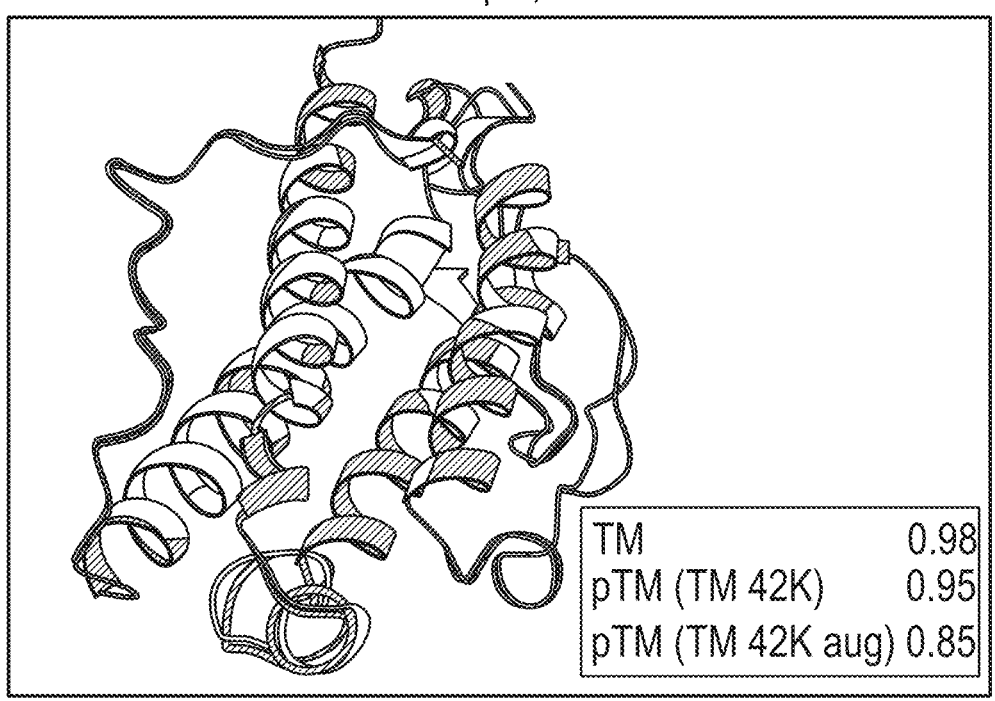
FIGS. 4A-4C are visualizations of a predicted protein structure (crosshatched) in combination with a ground truth 3D protein structure (hollow), in accordance with an example embodiment.
Figure 4B:
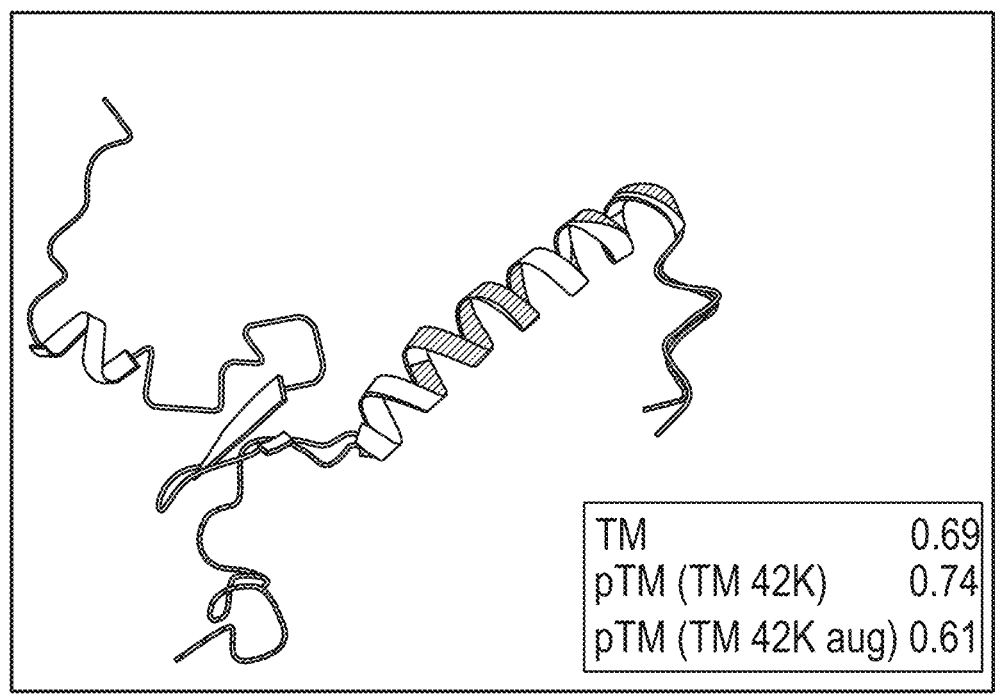
Figure 4C:
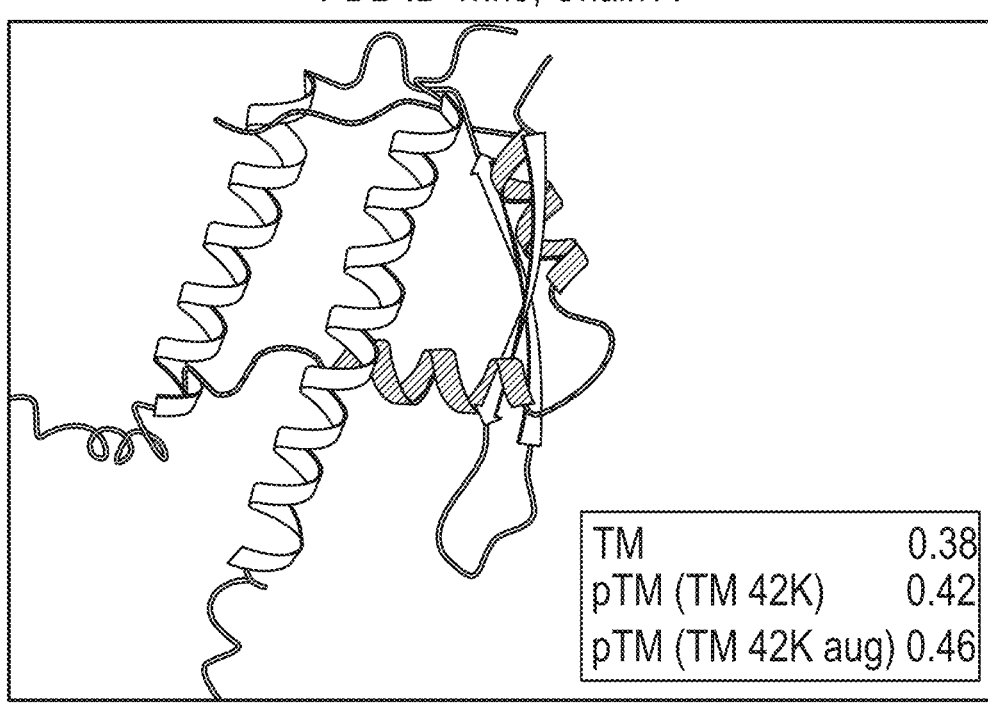

In FIG. 3C, scatter plots of the true TM score vs pTM scores and pLDDT values on the entire validation set are shown. A clear diagonal pattern is seen in both plots, where the predicted and true values match. In FIGS. 4A-4C, a few examples of the 3D protein structures from the dataset are shown together with the corresponding predicted structures generated by the distilled model 212. FIG. 3C also shows plots of SC (pTM or pLDDT) versus TM score, indicating that the distilled model 212 is a viable tool for regularizing protein representation to enforce structural consistency or structural scoring of protein sequences, reflecting its overall composition and naturalness (in terms of plausible folded structure).

FIG. 3B is a table showing the validation CE loss for a variety of example datasets, in accordance with an example embodiment. The distilled model 212 was initialized with the weights of the conventional protein version of a BERT model. As illustrated in the table of FIG. 3B, the distilled model 212 generated with the TM 42K dataset has the lowest CE loss (1.10).

Examples of Data and the Predictions

FIGS. 4A-4C are visualizations of example protein structures from the identified dataset, corresponding to high, medium, and low actual TM scores (top row in the legends), as well as predictions of the distilled model 212, trained on the TM 42K dataset (middle row) and the TM augmented 86K dataset (bottom row), in accordance with an example embodiment. Scores were generated using the distilled model 212. Higher values indicate a higher match between the predicted protein structure and the ground truth 3D protein structure.

Figure 5A:
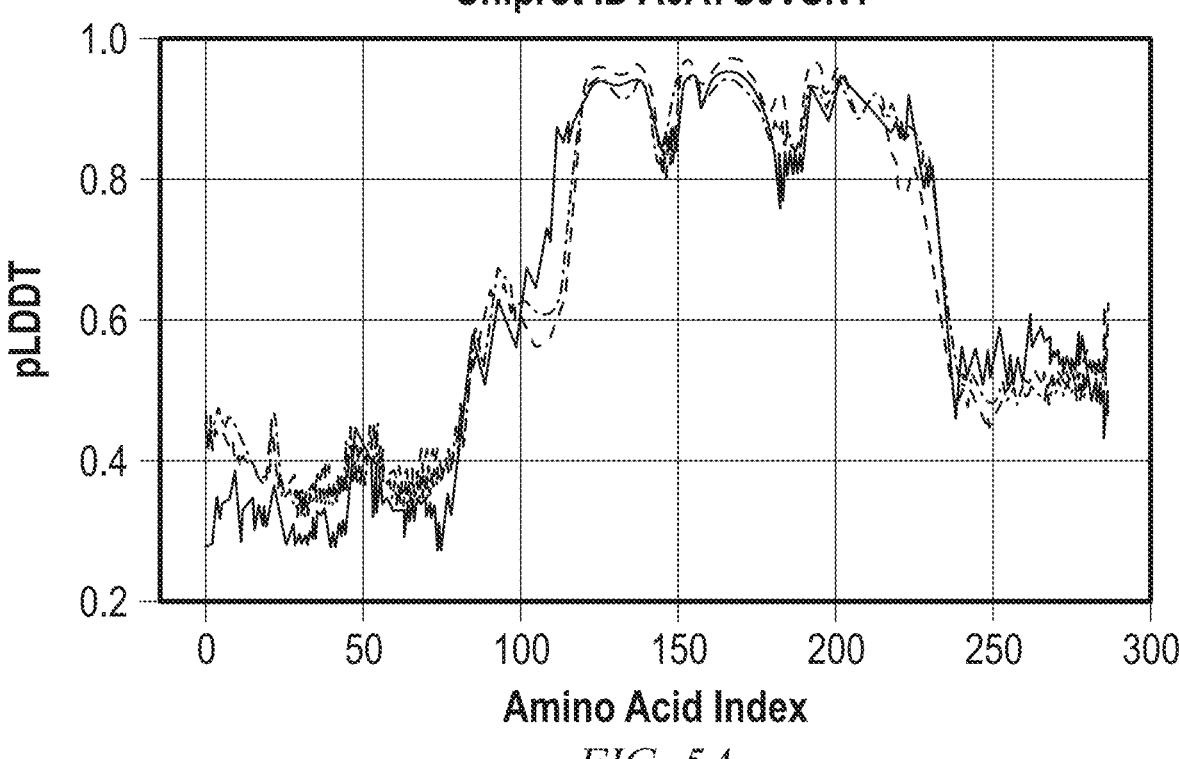
FIGS. 5A-5C are graphs of the predicted predictive Local Distance Difference Test (pLDDT) metric vs. each amino acid position of the protein of FIGS. 4A-4C, respectively, in accordance with an example embodiment.
Figure 5B:
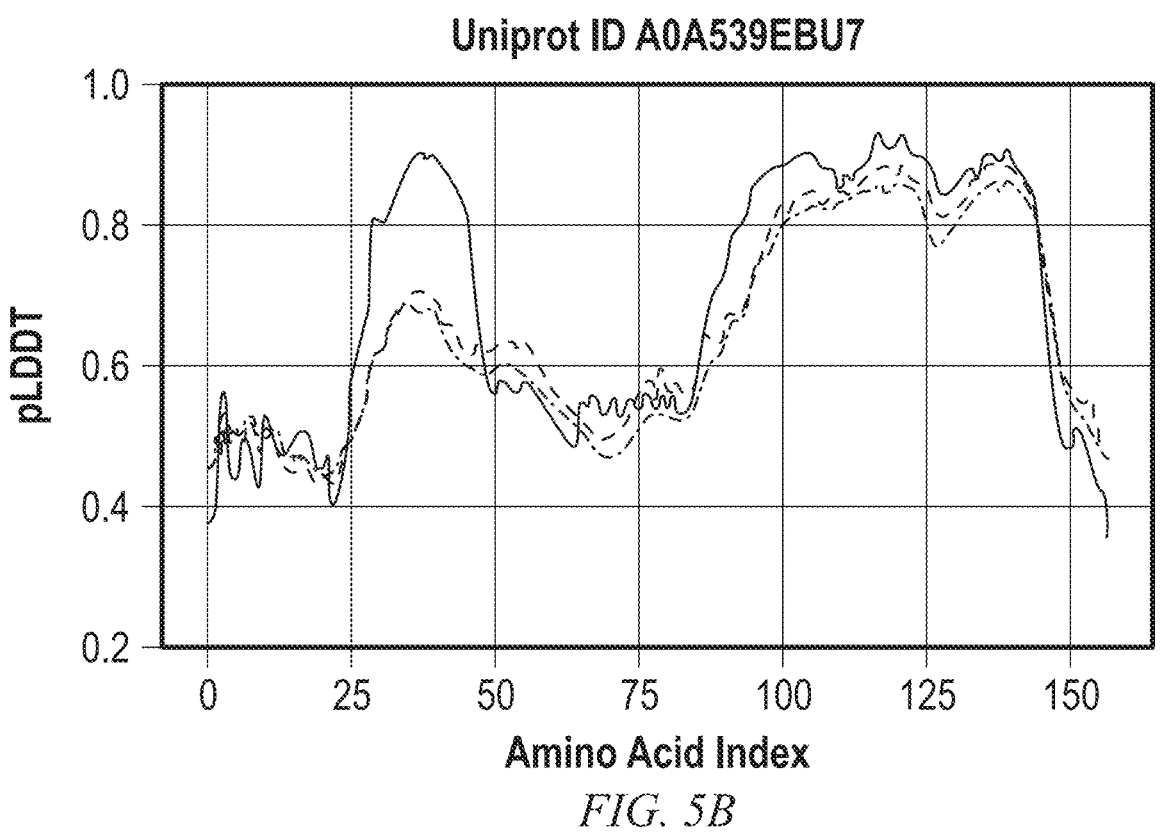
Figure 5C:
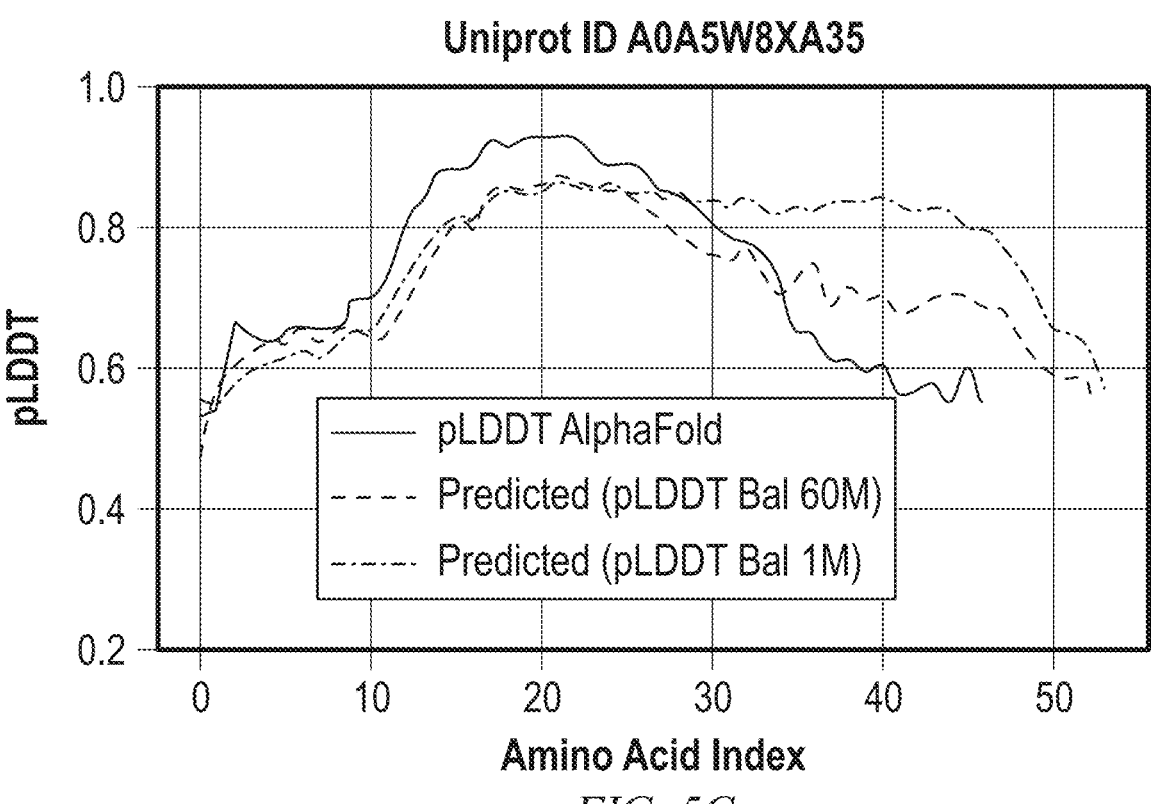

FIGS. 5A-5C are graphs of the predicted pLDDT metric vs. each amino acid position of the protein of FIGS. 4A-4C, respectively, in accordance with an example embodiment. The LDDT metric assigns a value to each of the positions (amino acids) in the protein sequence indicating the quality of the match (numbers indicate how accurate the match is for the corresponding amino acid position where a match indicates a well-designed sequence). Smaller values mean a poorly designed 3D structure; higher values mean a well-designed 3D structure. The graphs of FIGS. 5A-5C correspond to dataset examples of the per-residue predictions for two distilled models 212 (dashed lines), built on the pLDDT balanced 1M and 60M datasets, versus the predictions of the conventional forward protein folding model 240 (solid line). The legend of FIG. 5C also applies for FIGS. 5A and 5B for the correlation of line style to dataset used.

Inverse Protein Folding

The benefit of applying the distilled model 212 as a structure consistency (SC) score 252 for solving the task of inverse protein folding is demonstrated below, as well as for the protein sequence infilling as a means to novel antibody generation. The overall framework is presented below in conjunction with FIG. 6A (indicated by the lowest dotted line in the diagram of FIG. 6A), where the new inverse folding model 616 that is being trained is regularized by the disclosed SC score 252. Specifically, during training of the new machine learning model, e.g., the inverse folding model 616, the generated protein 608 is fed into the distilled model 212, which causes the distilled model 212 to predict the pTM or pLDDT score, and combined with the original CE training objective results in the final loss 604 described below.

Figures 6A, 6B:
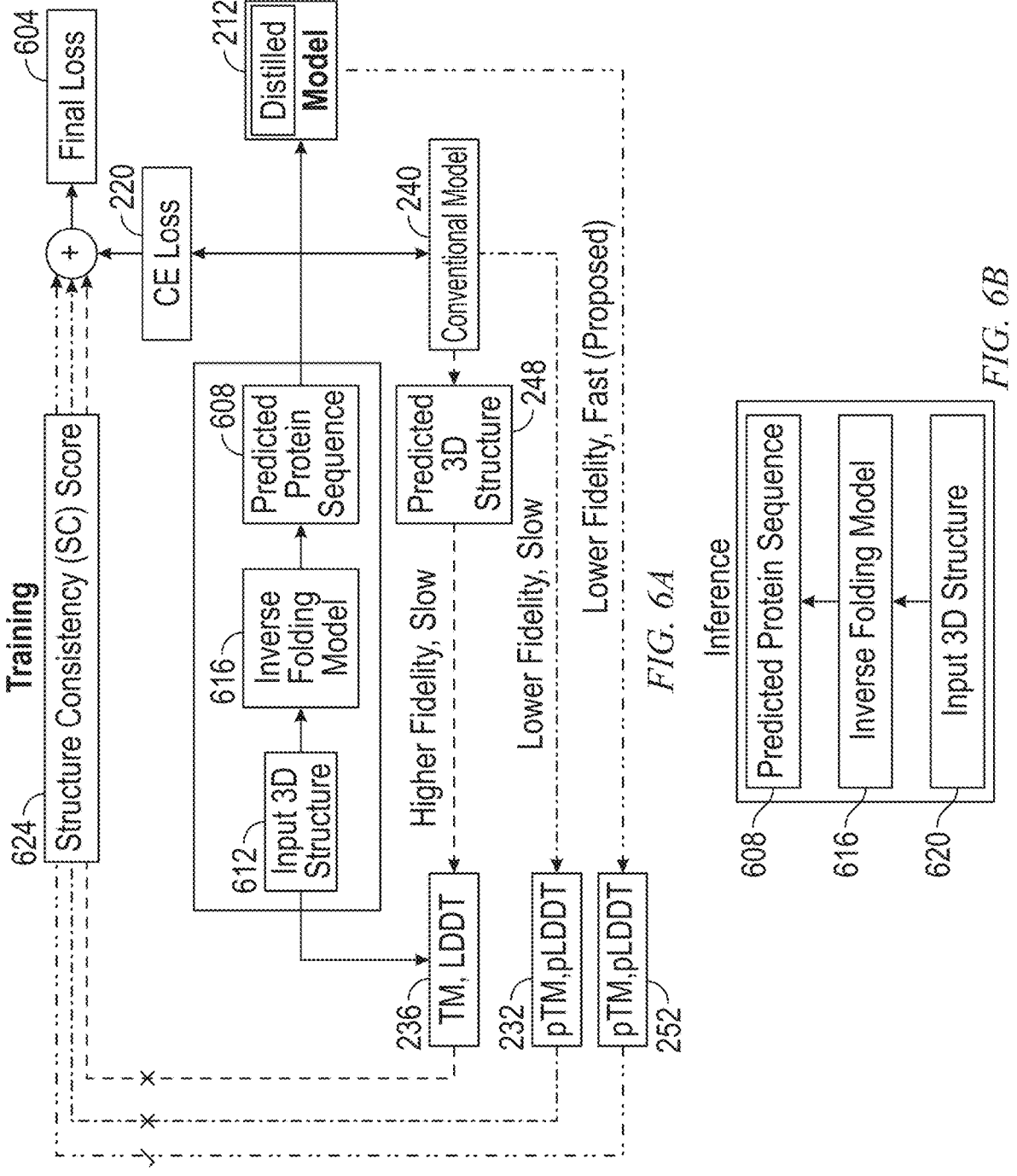
FIG. 6A is a block diagram of a system for improving an inverse folding machine learning model using the distilled model, in accordance with an example embodiment.
FIG. 6B is a block diagram of a system for performing inferencing using the trained inverse folding machine learning model of FIG. 6A, in accordance with an example embodiment.

FIG. 6A is a block diagram of a system for improving an inverse folding machine learning model 616 using the distilled model 212, in accordance with an example embodiment. In one example embodiment, an input 3D structure 612 is submitted to an inverse folding model 616 to generate a predicted protein sequence 608. The various input 3D structures 612 that are used in some embodiments are obtained from publicly available protein data banks. Such publicly available protein data banks contain information about millions of protein sequences. For a protein infilling task, the input 3D structure 612 represents an antibody (protein) structure. In some embodiments, this antibody (protein) structure is obtained from a publicly available antibody structure database. In the protein infilling task, the model 616 produces fillings for specific regions of a protein and/or antibody. The distilled model 212 processes the predicted protein sequence 608 to generate the predicted metrics 252 (see FIG. 1B). The structure consistency (SC) score 624 and the CE loss 220 are combined to generate the final loss 604. In one example embodiment, the structure consistency (SC) score 624 includes the predicted metrics 252 and the final loss 604 is defined as:

$$\mathcal{L} = \mathcal{L}_{CE} + \alpha \mathcal{L}_{SC}$$

where $$\mathcal{L}_{CE} = \sum\nolimits_{1}^{N} \mathcal{L}_{CE}(s_i, \hat{s}_i)$$

is a cross-entropy loss, $s_i$ is the ground truth, $\hat{s}_i$ is the generated protein sequence, $$\mathcal{L}_{SC} = \sum\nolimits_{i=1}^{N} (1 - SC(\hat{s}_i))$$

is the structure consistency (SC) score 624, N is the number of training sequences, and α is the weighting scalar for the SC loss (set to one in the present experiments). (The skilled artisan will recognize that the weight α may be determined heuristically and may be set, for example, to one.) The introduction of the structure consistency (SC) score 624 into the final loss 604 improves, for example, the accuracy and/or diversity of the resulting inverse folding machine learning model 616.

FIG. 6B is a block diagram of a system for performing inferencing using the trained inverse folding machine learning model 616 of FIG. 6A, in accordance with an example embodiment. Once trained, the inverse folding machine learning model 616, may be used to infer a predicted protein sequence 608. In one example embodiment, an input 3D structure 620 is submitted to the trained inverse folding machine learning model 616. The trained inverse folding machine learning model 616 then generates the predicted protein sequence 608.

It is noted that alternative configurations of FIG. 6A are also contemplated. For example, the conventional forward protein folding model 240 is used to process the predicted protein sequence 608. In a first case, the predicted metrics 232 produced by the conventional forward protein folding model 240 are used as a structure consistency (SC) score 624 for improving the inverse folding machine learning model 616; however, generating the predicted metrics 232 requires more processing power, more computing time ("slow"), and more computer resources (for storing the larger conventional forward protein folding model 240) in comparison to the distilled model 212. Moreover, the predicted metrics 232 are characterized by a lower fidelity. In addition, the final loss using the predicted metrics 232 is non-differentiable (meaning gradient descent algorithms cannot be used to optimize the model parameters).

In a second case, the predicted 3D structure 248 and the metrics 236 are generated by the conventional forward protein folding model 240 and the produced metrics 236 are used as a structure consistency (SC) score 624 for improving the inverse folding machine learning model 616; however, generating the metrics 236 requires more processing power, more computing time ("slow"), and more computer resources (for storing the larger conventional forward protein folding model 240) in comparison to the distilled model 212. In addition, the final loss using the metrics 236 is non-differentiable.

Metrics

To measure the quality of the prediction designs, the following set of sequence evaluation metrics were computed. Recovery (range (0, 100) where higher is better) is the average number of exact matches between the predicted and the ground truth sequences, normalized by the length of the alignment. Diversity (range (0, 100) where higher is better) of a predicted protein set is the complement of the average recovery computed for all pairwise comparisons in the set. While in general the recovery and diversity tend to be inversely correlated (that is, higher recovery leads to lower diversity, and vice versa), a primary interest is in models that achieve high recovery rates and are able to maintain high protein sequence diversity. Diversity helps to build a more diverse training dataset (where a high level of diversity is desired). Perplexity measures the likelihood of a given sequence, where lower values indicates better performance. For structure evaluation, the TM-score was used as well as the structure consistency (SC) score 252 which is the output (pTM/pLDDT) of the distilled model 212 for a given input.

Results

Experimental results are presented for several recently proposed deep generative models for protein sequence design accounting for 3D structural constraints. For the inverse folding tasks, the classification of protein structures dataset was used. The training, validation, and test sets have 18204, 608, and 1120 structures, respectively. While for protein infilling, a conventional structural antibody dataset was used with a focus on infilling CDR-H3 (the most diverse region in antibodies) loop. The dataset has 3896 training, 403 validation and 437 test sequences.

Figure 7:
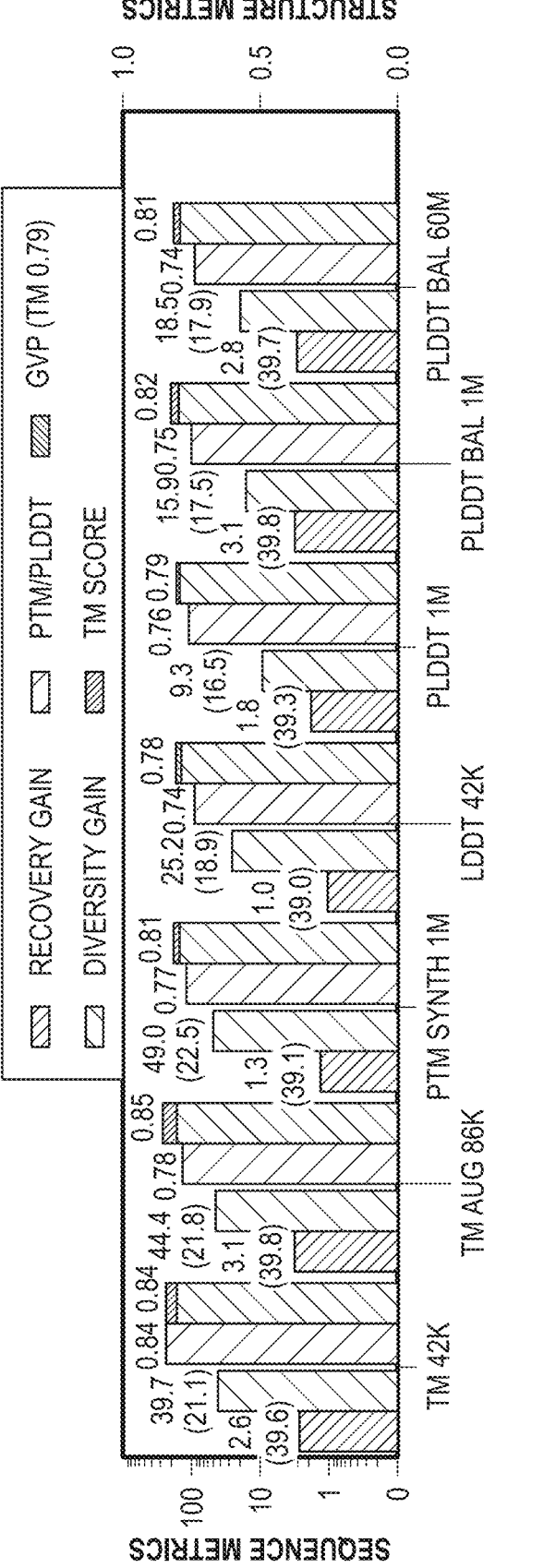
FIG. 7 is a bar chart illustrating various metrics generated for a conventional inverse protein folding task for a variety of datasets, in accordance with example embodiments.

FIG. 7 is a bar chart illustrating various metrics generated for a conventional inverse protein folding task trained with SC regularization for a variety of datasets, in accordance with example embodiments. The metrics include the recovery gain, diversity gain, pTM/pLDDT, and the TM score. The horizontal x-axis shows various datasets for pretraining the distilled model 212, the left vertical y-axis shows sequence metrics (recovery and diversity gains), while the right y-axis shows structure metrics (TM and SC scores). Cross-hatched bars show recovery and diversity gains (top number is a percentage; bottom number is the actual value) of a SC-regularized inverse protein folding task over the conventional inverse protein folding task baseline. Solid black bar shows the predicted SC (pTM or pLDDT, depending on the distilled model 212), while the hollow bar of each set is the test set TM score (structures predicted by large conventional forward protein folding model). The dashed bar overlaid on the hollow bar is the TM score of the baseline conventional forward protein folding model. It can be seen that the overall TM 42K and TM augmented 86K pretrained distilled models 212 achieve the best overall performance, with high diversity and moderate improvement in sequence and structure recovery. Improvements over the baseline of the conventional inverse protein folding task are shown for all metrics and all datasets (baseline: recovery of 38.6, diversity of 15.1, and TM score of 0.79).

A conventional rotation-equivariant graph neural network (GNN) is the inverse folding model that, for a given target backbone structure, represented as a graph over the residues, replaces dense layers in a GNN by simpler layers, called geometric vector perceptrons (GVP) layers, directly leveraging both scalar and geometric features. This usage of the GVSP layers allows for the embedding of geometric information at nodes and edges without reducing such information to scalars that may not fully capture complex geometry. The results of augmenting training of the conventional rotation-equivariant GNN with SC score regularization are shown in FIG. 7. The baseline conventional rotation-equivariant GNN with no regularization achieves 38.6 in recovery, 15.1 in diversity and 0.79 in TM score on the test set. It can be seen that there is a consistent improvement in sequence recovery gain (1-3%) over the original the conventional rotation-equivariant GNN and significant diversity gain (up to 45%) of the generated protein sequences when SC regularization is employed. At the same time, the estimated structure (using the large conventional forward protein folding model) remains close to the original as measured by the high TM score. It was also observed that pTM-based SC scores had overall better influence on the model performance as compared to pLDDT-based ones. It should be further noted that the validation performance of the distilled model 212 on the distillation data is not always reflective of the performance on the downstream applications, as distilled model 212 trained on the TM augmented 86K dataset overall performs better than the TM 42K dataset, while having slightly worse validation CE loss (see the table of FIG. 3B). This observation indicates that the augmented models might be less biased by the teacher model, hence enables more generalized representation learning of the sequence-structure relationship and provides more performance boost to the inverse folding model.

To further illustrate the effect of recovery and diversity, protein sequences and generated 3D structures of the conventional rotation-equivariant GNN and the conventional rotation-equivariant GNN with SC models are shown in FIGS. 4A-4C and 5A-5C, where the latter model achieves higher diversity of the sequence while retaining accurate structure of the original protein. Here, the recovery is 40.8 and diversity is 11.2 for the conventional rotation-equivariant GNN, while for the conventional rotation-equivariant GNN with SC it is 42.8 and 22.6, respectively, confirming that the conventional rotation-equivariant GNN with SC achieves higher recovery and diversity. FIGS. 4A-4C show estimated structures of the large conventional forward protein folding model (crosshatched) and the ground truth (hollow). It can be seen that for the conventional rotation-equivariant GNN with SC, the high sequence diversity still results in very accurate reconstructions (for this example, the average TM score is 0.95), while the conventional rotation-equivariant GNN alone shows more inconsistencies, marked with arrows (TM score is 0.92).

Figure 8A:
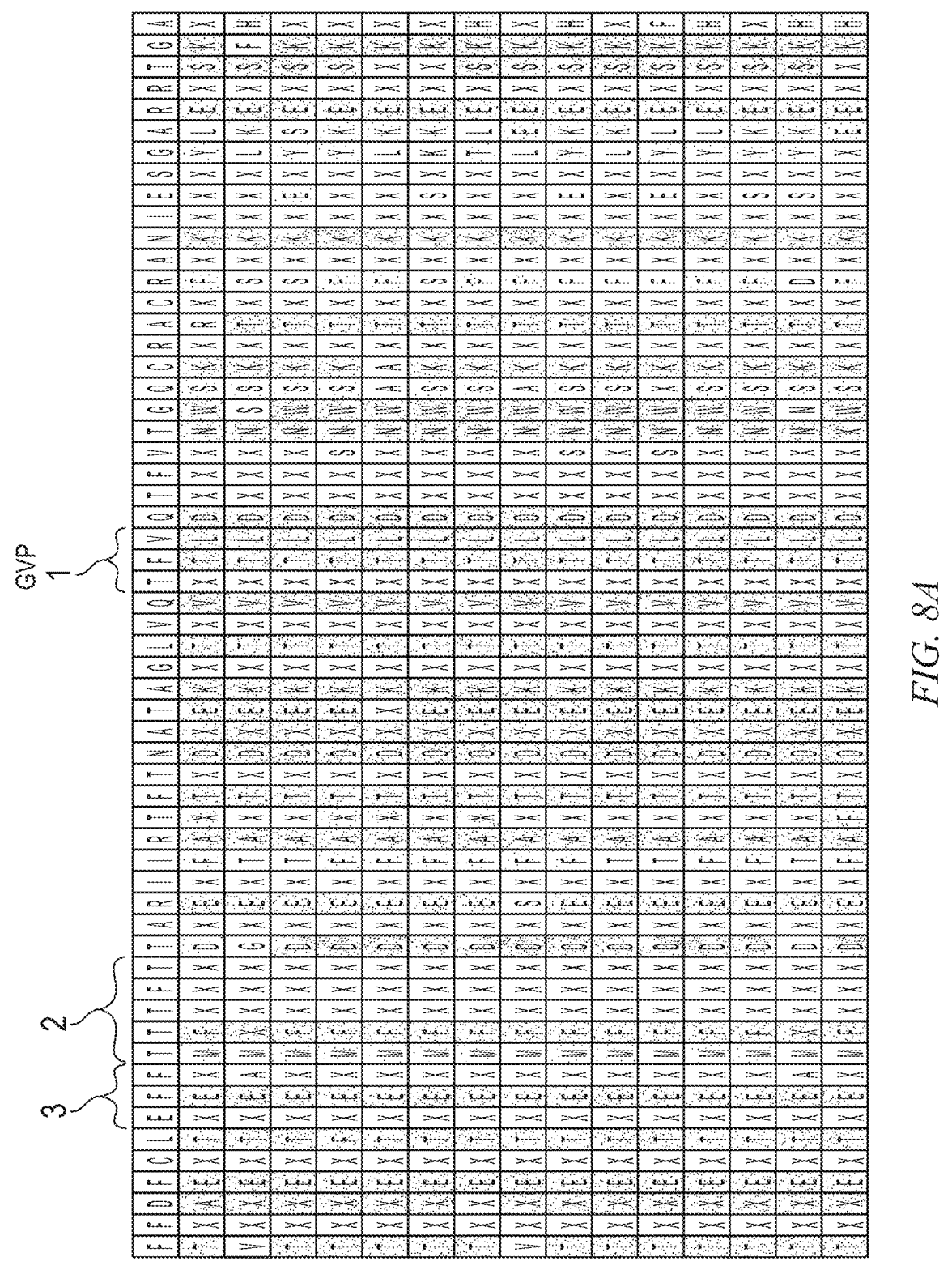
Figure 8B:
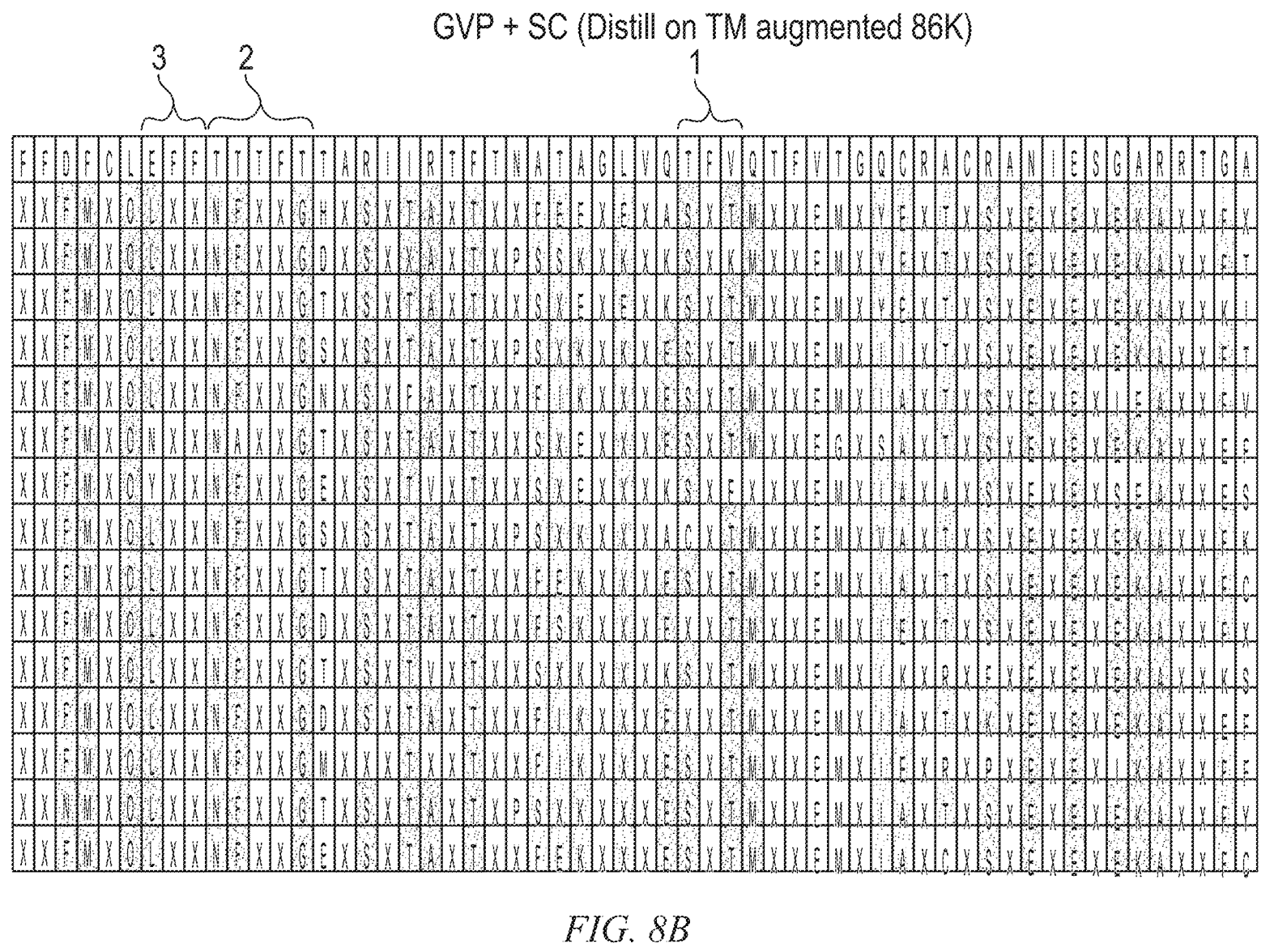
Figure 8C:
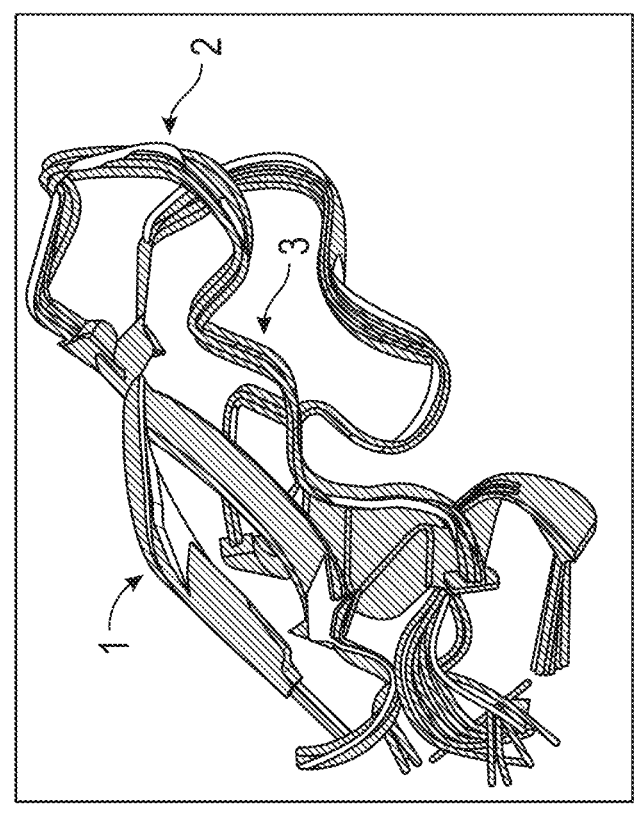
FIG. 8C shows visualizations of a predicted protein structure (crosshatched) in combination with a ground truth 3D protein structure (hollow) for the matrices of FIGS. 8A-8B, in accordance with an example embodiment.
Figure 8C:
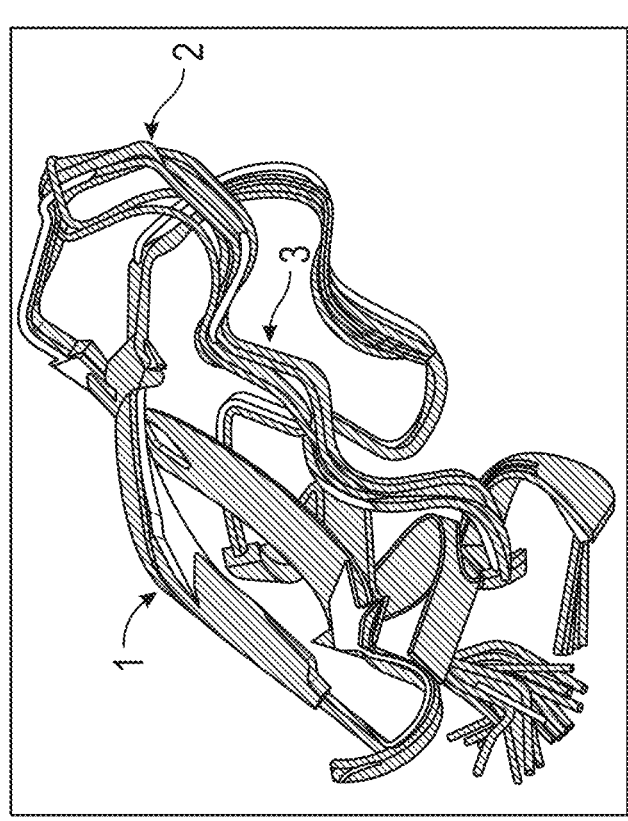

FIGS. 8A and 8B together show a comparison between a baseline inverse folding model (FIG. 8A) and a SC regularized inverse folding model (FIG. 8B), where the distilled model 212 was pretrained on the TM augmented 86K dataset, and used for the SC regularization in FIG. 8B, in accordance with an example embodiment. The tables display 15 generated protein sequences from each model (the top row is the ground truth). Hollow cells with the * indicate amino acid identity compared to the ground truth (top row), while dotted cells show novelty. The intensity of the dots of each dotted cell represents the frequency of the amino acid in that column (more dots indicates more frequent; fewer dots indicates less frequent (rare)). Therefore, the method with high recovery and diversity rates will have many hollow and lightly dotted cells. FIG. 8C shows the estimated structures (crosshatched) and the ground truth (hollow) of the large conventional forward protein folding model. The left drawings of FIG. 8C are the estimated structures resulting from GVP usage corresponding to FIG. 8A. The right drawings of FIG. 8B are the estimated structures resulting from the SC-regularized GVP corresponding to FIG. 8B according to embodiments of the invention. One example SC-regularized inverse folding model, while having high sequence diversity, still results in accurate reconstructions, while the original corresponding inverse folding model alone has more inconsistencies, marked with arrows.

Figures 9, 10:
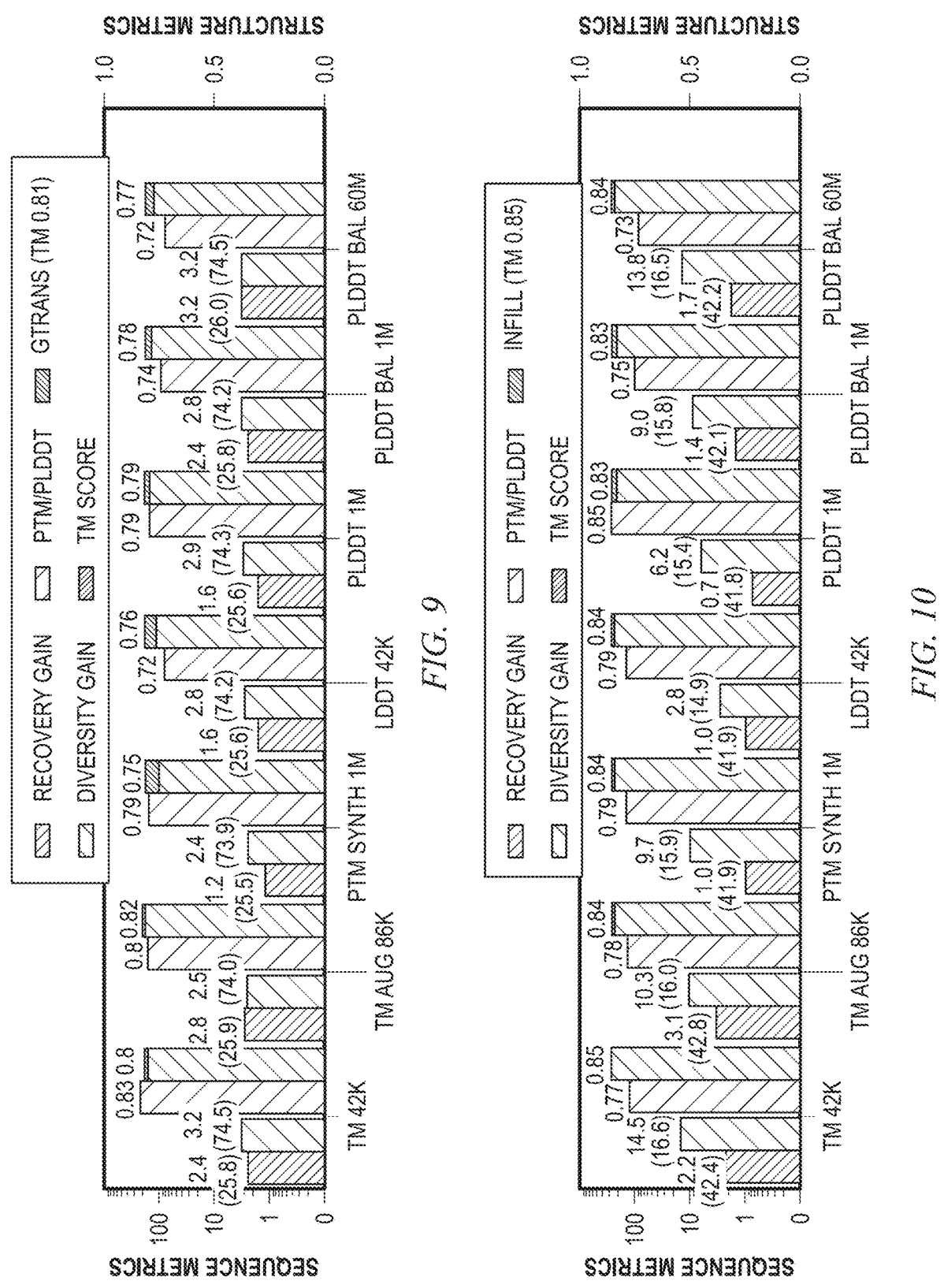
FIG. 9 is a bar chart illustrating various metrics generated for a conventional graph transformer task for a variety of datasets, in accordance with example embodiments.
FIG. 10 is a bar chart illustrating various metrics generated for a conventional protein infilling task for a variety of datasets, in accordance with example embodiments.

Graph Transformer: The effect of the SC score 252 on a conventional graph transformer, another inverse folding model, which seeks to improve standard GNNs to represent the protein 3D structure was evaluated. A graph transformer applies a permutation-invariant transformer module after a GNN module to better represent the long-range pair-wise interactions between the graph nodes. The results of augmenting training of the graph transformer with the SC score regularization are shown in FIG. 9. A baseline model with no regularization has 25.2 in recovery, 72.2 in diversity and 0.81 in the TM score on the test set. As compared to the conventional rotation-equivariant GNN (see FIG. 7), it can be seen that, for this model, the recovery and diversity gains upon SC regularization are smaller. It is also seen that the TM score of the regularized model (with TM 42K and TM augmented 86K pretraining) is slightly higher as compared to pLDDT-based models.

FIG. 9 is a bar chart illustrating various metrics generated for a conventional graph transformer task trained with SC regularization for a variety of datasets, in accordance with example embodiments. The metrics include the recovery gain, diversity gain, pTM/pLDDT, and the TM score. Improvements over the baseline of the conventional graph transformer task are shown for all metrics and all datasets (baseline: recovery of 25.2, diversity of 72.2, and TM score of 0.81).

Complementarity-Determining Region (CDR)

Exemplary embodiments of structure consistency regularization are quite general and not limited to the inverse folding task. Here, its application is shown on a protein infilling task. Recall, that while the inverse folding task considers generating the entire protein sequence, conditioned on a given structure, infilling focuses on filling specific regions of a protein conditioned on a sequence/structure template. The complementarity-determining regions (CDRs) of an antibody protein are of particular interest as they determine the antigen binding affinity and specificity. A conventional framework which formulates the problem as generation of the CDRs conditioned on a fixed framework region is followed. One focus is on CDR-H3 and a baseline pretrained conventional protein model finetuned on the infilling dataset is used, and the baseline pretrained conventional protein model with SC is used as an alternative (finetuned with SC regularization). The CDR-H3 is masked and the objective is to reconstruct it using the rest of the protein sequence as a template. The results are shown in FIG. 10. Baseline model achieves 41.5 in recovery, 14.5 in diversity, and 0.80 in TM score on the test set. Similar as for the other applications, an improvement in the sequence recovery and even bigger gain in diversity are seen, while using the distilled model 212 pretrained on the TM 42K and TM augmented 86K datasets, together with the pLDDT balanced datasets. The TM score shows that the resulting 3D structure remains close to the original, confirming the benefit of using SC for training regularization.

FIG. 10 is a bar chart illustrating various metrics generated for a conventional protein infilling task trained with SC regularization for a variety of datasets, in accordance with example embodiments. Infilling is often used in the design of antibodies where some portion of the protein sequence is missing. In one example embodiment, the task is infill CDR-H3 (the most diverse region in antibodies) using sequence information only. (CDR (protein infilling) is the region that attaches to the antigen (virus).) The metrics include the recovery gain, diversity gain, pTM/pLDDT, and the TM score. Improvements over the baseline of the conventional graph transformer task are shown for all metrics and all datasets (baseline: recovery of 41.5, diversity of 14.5, and TM score of 0.80).

Techniques as disclosed herein can provide substantial beneficial technical effects. Some embodiments may not have these potential advantages and these potential advantages are not necessarily required of all embodiments. By way of example only and without limitation, one or more embodiments may provide one or more of:

improves the technological process of machine learning by generating more accurate machine learning models using a smaller, faster training model that has been distilled from a larger, slower training model;

savings in running time, processing resources and memory resources by using the smaller, faster distilled training model to train a machine learning model of a downstream application;

improved inverse folding machine learning models;

a small, accurate, end-to-end differentiable machine learning model to score protein sequences;

model and techniques for regularizing inverse protein folding tasks, protein infilling applications, and other downstream applications;

techniques that improve recovery protein folding tasks (the generated protein sequence and the ground truth protein sequence match well where many amino acids in the corresponding positions coincide); and techniques that improve diversity-regarding protein folding tasks (if several protein sequences are generated, each sequence will be different from the other one, a positive effect).

Given the discussion thus far, it will be appreciated that, in general terms, an exemplary method, according to an aspect of the invention, includes the operations of initializing, using at least hardware processor, a distilled model 212 with initial weights; inputting, using the at least hardware processor, an input protein sequence 208 into both the distilled model 212 and a folding protein model 240; generating, using the at least hardware processor and the distilled model 212, logits 216; generating, using the at least hardware processor and the folding protein model 240, one or more predictive metrics 252; discretizing, using the at least hardware processor, the one or more predictive metrics 232 into classes 224; computing, using the at least hardware processor, a cross-entropy loss 220 based on the logits 216 and the classes 224; training, using the at least hardware processor, the distilled model 212 based on the cross-entropy loss 220; and training a machine learning model 616 of a downstream protein modeling task using the trained distilled model 212.

In one example embodiment, a protein is designed using the machine learning model 616 and the protein designed using the machine learning model 616 is synthesized.

In one example embodiment, the machine learning model 616 for the downstream protein modeling task is accessed, the machine learning model 616 being trained with computer-generated inverse folding proteins and computer-generated forward folding proteins; and a synthetic protein sequence is generated based on an inversely folded protein generated using the machine learning model 616.

In one example embodiment, the training the machine learning model of the downstream protein modeling task is based on a final loss 604, wherein the final loss 604 is based on the predictive metrics 252 and the cross-entropy loss 220.

In one example embodiment, the downstream protein modeling task is an inverse protein folding task and the final loss 604 regularizes the inverse protein folding task.

In one example embodiment, the downstream protein modeling task is a protein infilling task and the final loss 604 regularizes the inverse protein infilling task.

In one example embodiment, the final loss 604 is defined as:

$$\mathcal{L} = \mathcal{L}_{CE} + \alpha \mathcal{L}_{SC}$$

where $$\mathcal{L}_{CE} = \sum_{1}^{N} \mathcal{L}_{CE}(s_i, \hat{s}_i)$$

is a cross-entropy loss, $s_i$ is a ground truth, $\hat{s}_i$ is a generated protein sequence, $$\mathcal{L}_{SC} = \sum_{i=1}^{N} (1 - SC(\hat{s}_i))$$

is the structure consistency (SC) score 624, N is a number of training sequences, and a is a weighting scalar for the structure consistency (SC) score 624.

In one aspect, a computer program product comprises one or more tangible computer-readable storage media and program instructions stored on at least one of the one or more tangible computer-readable storage media, the program instructions executable by a processor, the program instructions comprising initializing a distilled model 212 with initial weights; inputting an input protein sequence 208 into both the distilled model 212 and a folding protein model 240; generating, using the distilled model 212, logits 216; generating, using the folding protein model 240, one or more predictive metrics 252; discretizing the one or more predictive metrics 232 into classes 224; computing a cross-entropy loss 220 based on the logits 216 and the classes 224; training the distilled model 212 based on the cross-entropy loss 220; and training a machine learning model 616 of a downstream protein modeling task using the trained distilled model 212.

In one aspect, an apparatus comprises a memory and at least one processor, coupled to the memory, and operative to perform operations comprising initializing a distilled model 212 with initial weights; inputting an input protein sequence 208 into both the distilled model 212 and a folding protein model 240; generating, using the distilled model 212, logits 216; generating, using the folding protein model 240, one or more predictive metrics 252; discretizing the one or more predictive metrics 232 into classes 224; computing a cross-entropy loss 220 based on the logits 216 and the classes 224; training the distilled model 212 based on the cross-entropy loss 220; and training a machine learning model 616 of a downstream protein modeling task using the trained distilled model 212.

Given the discussion thus far, it will be appreciated that, in general terms, an exemplary method, according to an aspect of the invention, includes the operations of producing a distilled machine learning model 212 via: initializing a first model with initial weights; inputting an input protein sequence 208 into both the first model and a folding protein model 240, wherein the inputting to the first model generates logits 216, and wherein the inputting to the folding protein model 240 generates one or more predictive metrics; discretizing the one or more predictive metrics into classes 224; computing a first cross-entropy loss 220 based on the logits 216 and the classes 224; and optimizing the first model based on the first cross-entropy loss 220 so that the optimized first model is the distilled machine learning model 212; and training, using the distilled machine learning model 212, an additional machine learning model 616 to perform a downstream protein modeling task.

In one example embodiment, a protein design is produced using the trained additional machine learning model 616 and a protein is synthesized based on the protein design.

In one example embodiment, the training of the additional machine learning model 616 comprises inputting, separately, protein structures into the additional machine learning model 616, wherein, in response, the additional machine learning model 616 generates as output a respective predicted protein sequence corresponding to the input protein structures.

In one example embodiment, the training of the additional machine learning model 616 comprises feeding output from the additional machine learning model 616 to the distilled machine learning model 212, wherein the distilled machine learning model 212, in response, generates a structure consistency score 624; and optimizing the additional machine learning model 616 based on a second cross entropy loss and on a loss of the structure consistency score 624, wherein the second cross entropy loss is based on a ground truth value of the output of the additional machine learning model 616.

In one example embodiment, the output of the additional machine learning model 616 comprises a protein design.

In one example embodiment, the downstream protein modeling task comprises an inverse protein folding task and the structure consistency score 624 regularizes the inverse protein folding task.

In one example embodiment, the downstream protein modeling task comprises a protein infilling task and the structure consistency score 624 regularizes the protein infilling task.

In one example embodiment, the folding protein model infers protein structure based on a protein sequence that is input, comprises a deep learning model and an attention network, was trained from a public repository of protein sequences and structures, and is larger than the distilled machine learning model 212.

In one example embodiment, the producing a distilled machine learning model 212 further comprises generating a set of one or more metrics via a ground truth three-dimensional structure; and discretizing the set of the one or more metrics into the classes 224 such that the cross-entropy loss 220 is further based on the one or more metrics.

In one aspect, a computer program product comprises one or more tangible computer-readable storage media and program instructions stored on at least one of the one or more tangible computer-readable storage media, the program instructions executable by a processor to cause the processor to perform operations comprising producing a distilled machine learning model 212 via: initializing a first model with initial weights; inputting an input protein sequence 208 into both the first model and a folding protein model 240, wherein the inputting to the first model generates logits 216, and wherein the inputting to the folding protein model 240 generates one or more predictive metrics; discretizing the one or more predictive metrics into classes 224; computing a first cross-entropy loss 220 based on the logits 216 and the classes 224; and optimizing the first model based on the first cross-entropy loss 220 so that the optimized first model is the distilled machine learning model 212; and training, using the distilled machine learning model 212, an additional machine learning model 616 to perform a downstream protein modeling task.

In one aspect, an apparatus comprises a memory and at least one processor, coupled to the memory, and operative to perform operations comprising producing a distilled machine learning model 212 via: initializing a first model with initial weights; inputting an input protein sequence 208 into both the first model and a folding protein model 240, wherein the inputting to the first model generates logits 216, and wherein the inputting to the folding protein model 240 generates one or more predictive metrics; discretizing the one or more predictive metrics into classes 224; computing a first cross-entropy loss 220 based on the logits 216 and the classes 224; and optimizing the first model based on the first cross-entropy loss 220 so that the optimized first model is the distilled machine learning model 212; and training, using the distilled machine learning model 212, an additional machine learning model 616 to perform a downstream protein modeling task.

Refer now to FIG. 11.

Various aspects of the present disclosure are described by narrative text, flowcharts, block diagrams of computer systems and/or block diagrams of the machine logic included in computer program product (CPP) embodiments. With respect to any flowcharts, depending upon the technology involved, the operations can be performed in a different order than what is shown in a given flowchart. For example, again depending upon the technology involved, two operations shown in successive flowchart blocks may be performed in reverse order, as a single integrated step, concurrently, or in a manner at least partially overlapping in time.

A computer program product embodiment ("CPP embodiment" or "CPP") is a term used in the present disclosure to describe any set of one, or more, storage media (also called "mediums") collectively included in a set of one, or more, storage devices that collectively include machine readable code corresponding to instructions and/or data for performing computer operations specified in a given CPP claim. A "storage device" is any tangible device that can retain and store instructions for use by a computer processor. Without limitation, the computer readable storage medium may be an electronic storage medium, a magnetic storage medium, an optical storage medium, an electromagnetic storage medium, a semiconductor storage medium, a mechanical storage medium, or any suitable combination of the foregoing. Some known types of storage devices that include these mediums include: diskette, hard disk, random access memory (RAM), read-only memory (ROM), erasable programmable read-only memory (EPROM or Flash memory), static random access memory (SRAM), compact disc read-only memory (CD-ROM), digital versatile disk (DVD), memory stick, floppy disk, mechanically encoded device (such as punch cards or pits/lands formed in a major surface of a disc) or any suitable combination of the foregoing. A computer readable storage medium, as that term is used in the present disclosure, is not to be construed as storage in the form of transitory signals per se, such as radio waves or other freely propagating electromagnetic waves, electromagnetic waves propagating through a waveguide, light pulses passing through a fiber optic cable, electrical signals communicated through a wire, and/or other transmission media. As will be understood by those of skill in the art, data is typically moved at some occasional points in time during normal operations of a storage device, such as during access, de-fragmentation or garbage collection, but this does not render the storage device as transitory because the data is not transitory while it is stored.

Computing environment 100 contains an example of an environment for the execution of at least some of the computer code involved in performing the inventive methods, such as machine learning model distillation system 200 configured, for example, to control chemical processing equipment via WAN 102 to synthesize molecules and the like. In addition to block 200, computing environment 100 includes, for example, computer 101, wide area network (WAN) 102, end user device (EUD) 103, remote server 104, public cloud 105, and private cloud 106. In this embodiment, computer 101 includes processor set 110 (including processing circuitry 120 and cache 121), communication fabric 111, volatile memory 112, persistent storage 113 (including operating system 122 and block 200, as identified above), peripheral device set 114 (including user interface (UI) device set 123, storage 124, and Internet of Things (IoT) sensor set 125), and network module 115. Remote server 104 includes remote database 130. Public cloud 105 includes gateway 140, cloud orchestration module 141, host physical machine set 142, virtual machine set 143, and container set 144.

COMPUTER 101 may take the form of a desktop computer, laptop computer, tablet computer, smart phone, smart watch or other wearable computer, mainframe computer, quantum computer or any other form of computer or mobile device now known or to be developed in the future that is capable of running a program, accessing a network or querying a database, such as remote database 130. As is well understood in the art of computer technology, and depending upon the technology, performance of a computer-implemented method may be distributed among multiple computers and/or between multiple locations. On the other hand, in this presentation of computing environment 100, detailed discussion is focused on a single computer, specifically computer 101, to keep the presentation as simple as possible. Computer 101 may be located in a cloud, even though it is not shown in a cloud in FIG. 1. On the other hand, computer 101 is not required to be in a cloud except to any extent as may be affirmatively indicated.

PROCESSOR SET 110 includes one, or more, computer processors of any type now known or to be developed in the future. Processing circuitry 120 may be distributed over multiple packages, for example, multiple, coordinated integrated circuit chips. Processing circuitry 120 may implement multiple processor threads and/or multiple processor cores. Cache 121 is memory that is located in the processor chip package(s) and is typically used for data or code that should be available for rapid access by the threads or cores running on processor set 110. Cache memories are typically organized into multiple levels depending upon relative proximity to the processing circuitry. Alternatively, some, or all, of the cache for the processor set may be located "off chip." In some computing environments, processor set 110 may be designed for working with qubits and performing quantum computing.

Computer readable program instructions are typically loaded onto computer 101 to cause a series of operational steps to be performed by processor set 110 of computer 101 and thereby effect a computer-implemented method, such that the instructions thus executed will instantiate the methods specified in flowcharts and/or narrative descriptions of computer-implemented methods included in this document (collectively referred to as "the inventive methods"). These computer readable program instructions are stored in various types of computer readable storage media, such as cache 121 and the other storage media discussed below. The program instructions, and associated data, are accessed by processor set 110 to control and direct performance of the inventive methods. In computing environment 100, at least some of the instructions for performing the inventive methods may be stored in block 200 in persistent storage 113.

COMMUNICATION FABRIC 111 is the signal conduction path that allows the various components of computer 101 to communicate with each other. Typically, this fabric is made of switches and electrically conductive paths, such as the switches and electrically conductive paths that make up busses, bridges, physical input/output ports and the like. Other types of signal communication paths may be used, such as fiber optic communication paths and/or wireless communication paths.

VOLATILE MEMORY 112 is any type of volatile memory now known or to be developed in the future. Examples include dynamic type random access memory (RAM) or static type RAM. Typically, volatile memory 112 is characterized by random access, but this is not required unless affirmatively indicated. In computer 101, the volatile memory 112 is located in a single package and is internal to computer 101, but, alternatively or additionally, the volatile memory may be distributed over multiple packages and/or located externally with respect to computer 101.

PERSISTENT STORAGE 113 is any form of non-volatile storage for computers that is now known or to be developed in the future. The non-volatility of this storage means that the stored data is maintained regardless of whether power is being supplied to computer 101 and/or directly to persistent storage 113. Persistent storage 113 may be a read only memory (ROM), but typically at least a portion of the persistent storage allows writing of data, deletion of data and re-writing of data. Some familiar forms of persistent storage include magnetic disks and solid state storage devices. Operating system 122 may take several forms, such as various known proprietary operating systems or open source Portable Operating System Interface-type operating systems that employ a kernel. The code included in block 200 typically includes at least some of the computer code involved in performing the inventive methods.

PERIPHERAL DEVICE SET 114 includes the set of peripheral devices of computer 101. Data communication connections between the peripheral devices and the other components of computer 101 may be implemented in various ways, such as Bluetooth connections, Near-Field Communication (NFC) connections, connections made by cables (such as universal serial bus (USB) type cables), insertion-type connections (for example, secure digital (SD) card), connections made through local area communication networks and even connections made through wide area networks such as the internet. In various embodiments, UI device set 123 may include components such as a display screen, speaker, microphone, wearable devices (such as goggles and smart watches), keyboard, mouse, printer, touchpad, game controllers, and haptic devices. Storage 124 is external storage, such as an external hard drive, or insertable storage, such as an SD card. Storage 124 may be persistent and/or volatile. In some embodiments, storage 124 may take the form of a quantum computing storage device for storing data in the form of qubits. In embodiments where computer 101 is required to have a large amount of storage (for example, where computer 101 locally stores and manages a large database) then this storage may be provided by peripheral storage devices designed for storing very large amounts of data, such as a storage area network (SAN) that is shared by multiple, geographically distributed computers. IoT sensor set 125 is made up of sensors that can be used in Internet of Things applications. For example, one sensor may be a thermometer and another sensor may be a motion detector.

NETWORK MODULE 115 is the collection of computer software, hardware, and firmware that allows computer 101 to communicate with other computers through WAN 102. Network module 115 may include hardware, such as modems or Wi-Fi signal transceivers, software for packetizing and/or de-packetizing data for communication network transmission, and/or web browser software for communicating data over the internet. In some embodiments, network control functions and network forwarding functions of network module 115 are performed on the same physical hardware device. In other embodiments (for example, embodiments that utilize software-defined networking (SDN)), the control functions and the forwarding functions of network module 115 are performed on physically separate devices, such that the control functions manage several different network hardware devices. Computer readable program instructions for performing the inventive methods can typically be downloaded to computer 101 from an external computer or external storage device through a network adapter card or network interface included in network module 115.

WAN 102 is any wide area network (for example, the internet) capable of communicating computer data over non-local distances by any technology for communicating computer data, now known or to be developed in the future. In some embodiments, the WAN 102 may be replaced and/or supplemented by local area networks (LANs) designed to communicate data between devices located in a local area, such as a Wi-Fi network. The WAN and/or LANs typically include computer hardware such as copper transmission cables, optical transmission fibers, wireless transmission, routers, firewalls, switches, gateway computers and edge servers.

END USER DEVICE (EUD) 103 is any computer system that is used and controlled by an end user (for example, a customer of an enterprise that operates computer 101), and may take any of the forms discussed above in connection with computer 101. EUD 103 typically receives helpful and useful data from the operations of computer 101. For example, in a hypothetical case where computer 101 is designed to provide a recommendation to an end user, this recommendation would typically be communicated from network module 115 of computer 101 through WAN 102 to EUD 103. In this way, EUD 103 can display, or otherwise present, the recommendation to an end user. In some embodiments, EUD 103 may be a client device, such as thin client, heavy client, mainframe computer, desktop computer and so on.

REMOTE SERVER 104 is any computer system that serves at least some data and/or functionality to computer 101. Remote server 104 may be controlled and used by the same entity that operates computer 101. Remote server 104 represents the machine(s) that collect and store helpful and useful data for use by other computers, such as computer 101. For example, in a hypothetical case where computer 101 is designed and programmed to provide a recommendation based on historical data, then this historical data may be provided to computer 101 from remote database 130 of remote server 104.

PUBLIC CLOUD 105 is any computer system available for use by multiple entities that provides on-demand availability of computer system resources and/or other computer capabilities, especially data storage (cloud storage) and computing power, without direct active management by the user. Cloud computing typically leverages sharing of resources to achieve coherence and economies of scale. The direct and active management of the computing resources of public cloud 105 is performed by the computer hardware and/or software of cloud orchestration module 141. The computing resources provided by public cloud 105 are typically implemented by virtual computing environments that run on various computers making up the computers of host physical machine set 142, which is the universe of physical computers in and/or available to public cloud 105. The virtual computing environments (VCEs) typically take the form of virtual machines from virtual machine set 143 and/or containers from container set 144. It is understood that these VCEs may be stored as images and may be transferred among and between the various physical machine hosts, either as images or after instantiation of the VCE. Cloud orchestration module 141 manages the transfer and storage of images, deploys new instantiations of VCEs and manages active instantiations of VCE deployments. Gateway 140 is the collection of computer software, hardware, and firmware that allows public cloud 105 to communicate through WAN 102.

Some further explanation of virtualized computing environments (VCEs) will now be provided. VCEs can be stored as "images." A new active instance of the VCE can be instantiated from the image. Two familiar types of VCEs are virtual machines and containers. A container is a VCE that uses operating-system-level virtualization. This refers to an operating system feature in which the kernel allows the existence of multiple isolated user-space instances, called containers. These isolated user-space instances typically behave as real computers from the point of view of programs running in them. A computer program running on an ordinary operating system can utilize all resources of that computer, such as connected devices, files and folders, network shares, CPU power, and quantifiable hardware capabilities. However, programs running inside a container can only use the contents of the container and devices assigned to the container, a feature which is known as containerization.

PRIVATE CLOUD 106 is similar to public cloud 105, except that the computing resources are only available for use by a single enterprise. While private cloud 106 is depicted as being in communication with WAN 102, in other embodiments a private cloud may be disconnected from the internet entirely and only accessible through a local/private network. A hybrid cloud is a composition of multiple clouds of different types (for example, private, community or public cloud types), often respectively implemented by different vendors. Each of the multiple clouds remains a separate and discrete entity, but the larger hybrid cloud architecture is bound together by standardized or proprietary technology that enables orchestration, management, and/or data/application portability between the multiple constituent clouds. In this embodiment, public cloud 105 and private cloud 106 are both part of a larger hybrid cloud.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method comprising:
producing a distilled machine learning model via:
initializing a first model with initial weights;
inputting an input protein sequence into both the first model and a folding protein model, wherein the inputting to the first model generates logits, and wherein the inputting to the folding protein model generates one or more predictive metrics;
discretizing the one or more predictive metrics into classes;
computing a first cross-entropy loss based on the logits and the classes; and
optimizing the first model based on the first cross-entropy loss so that the optimized first model is the distilled machine learning model; and
training, using the distilled machine learning model, an additional machine learning model to perform a downstream protein modeling task.

2. The method of claim 1, further comprising:
producing a protein design using the trained additional machine learning model; and
synthesizing a protein based on the protein design.

3. The method of claim 2, wherein the training of the additional machine learning model comprises:
inputting, separately, protein structures into the additional machine learning model, wherein, in response, the additional machine learning model generates as output a respective predicted protein sequence corresponding to the input protein structures.

4. The method of claim 1, wherein the training of the additional machine learning model comprises:
feeding output from the additional machine learning model to the distilled machine learning model, wherein the distilled machine learning model, in response, generates a structure consistency score; and
optimizing the additional machine learning model based on a second cross entropy loss and on a loss of the structure consistency score, wherein the second cross entropy loss is based on a ground truth value of the output of the additional machine learning model.

5. The method of claim 4, wherein the output of the additional machine learning model comprises a protein design.

6. The method of claim 4, wherein the downstream protein modeling task comprises an inverse protein folding task and the structure consistency score regularizes the inverse protein folding task.

7. The method of claim 4, wherein the downstream protein modeling task comprises a protein infilling task and the structure consistency score regularizes the protein infilling task.

8. The method of claim 1, wherein the folding protein model:
infers protein structure based on a protein sequence that is input,
comprises a deep learning model and an attention network,
was trained from a public repository of protein sequences and structures, and
is larger than the distilled machine learning model.

9. The method of claim 1, wherein the producing a distilled machine learning model further comprises:
generating a set of one or more metrics via a ground truth three-dimensional structure; and
discretizing the set of the one or more metrics into the classes such that the cross-entropy loss is further based on the one or more metrics.

10. A computer program product, comprising:
one or more tangible computer-readable storage media and program instructions stored on at least one of the one or more tangible computer-readable storage media, the program instructions executable by a processor to cause the processor to perform operations comprising:
producing a distilled machine learning model via:
initializing a first model with initial weights;
inputting an input protein sequence into both the first model and a folding protein model, wherein the inputting to the first model generates logits, and wherein the inputting to the folding protein model generates one or more predictive metrics;
discretizing the one or more predictive metrics into classes;
computing a first cross-entropy loss based on the logits and the classes; and
optimizing the first model based on the first cross-entropy loss so that the optimized first model is the distilled machine learning model; and training, using the distilled machine learning model, an additional machine learning model to perform a downstream protein modeling task.

11. The computer program product of claim 10, the instructions further comprising:

producing a protein design using the trained additional machine learning model; and synthesizing a protein based on the protein design.

12. A system comprising:

a memory; and at least one processor, coupled to said memory, and operative to perform operations comprising:

producing a distilled machine learning model via:

initializing a first model with initial weights;

inputting an input protein sequence into both the first model and a folding protein model, wherein the inputting to the first model generates logits, and wherein the inputting to the folding protein model generates one or more predictive metrics;

discretizing the one or more predictive metrics into classes;

computing a first cross-entropy loss based on the logits and the classes; and optimizing the first model based on the first cross-entropy loss so that the optimized first model is the distilled machine learning model; and training, using the distilled machine learning model, an additional machine learning model to perform a downstream protein modeling task.

13. The system of claim 12, the operations further comprising:

producing a protein design using the trained additional machine learning model; and synthesizing a protein based on the protein design.

14. The system of claim 13, wherein the training of the additional machine learning model comprises:

inputting, separately, protein structures into the additional machine learning model, wherein, in response, the additional machine learning model generates as output a respective predicted protein sequence corresponding to the input protein structures.

15. The system of claim 12, wherein the training of the additional machine learning model comprises:

feeding output from the additional machine learning model to the distilled machine learning model, wherein the distilled machine learning model, in response, generates a structure consistency score; and optimizing the additional machine learning model based on a second cross entropy loss and on a loss of the structure consistency score, wherein the second cross entropy loss is based on a ground truth value of the output of the additional machine learning model.

16. The system of claim 15, wherein the output of the additional machine learning model comprises a protein design.

17. The system of claim 15, wherein the downstream protein modeling task comprises an inverse protein folding task and the structure consistency score regularizes the inverse protein folding task.

18. The system of claim 15, wherein the downstream protein modeling task comprises a protein infilling task and the structure consistency score regularizes the protein infilling task.

19. The system of claim 12, wherein the folding protein model:

infers protein structure based on a protein sequence that is input, comprises a deep learning model and an attention network, was trained from a public repository of protein sequences and structures, and is larger than the distilled machine learning model.

20. The system of claim 12, wherein the producing a distilled machine learning model further comprises:

generating a set of one or more metrics via a ground truth three-dimensional structure; and discretizing the set of the one or more metrics into the classes such that the cross-entropy loss is further based on the one or more metrics.

* * * * *